United States Patent
Chen et al.

(10) Patent No.: US 9,129,363 B2
(45) Date of Patent: Sep. 8, 2015

(54) METHOD FOR TEETH SEGMENTATION AND ALIGNMENT DETECTION IN CBCT VOLUME

(71) Applicant: Carestream Health, Inc., Rochester, NY (US)

(72) Inventors: Shoupu Chen, Rochester, NY (US); Lawrence A. Ray, Rochester, NY (US)

(73) Assignee: Carestream Health, Inc., Rochester, NY (US)

(*) Notice: Subject to any disclaimer, the term of this patent is extended or adjusted under 35 U.S.C. 154(b) by 10 days.

(21) Appl. No.: 13/949,281

(22) Filed: Jul. 24, 2013

(65) Prior Publication Data

US 2013/0308846 A1 Nov. 21, 2013

Related U.S. Application Data

(63) Continuation-in-part of application No. 13/448,466, filed on Apr. 17, 2012, now Pat. No. 8,842,904, and a continuation-in-part of application No. 13/187,596, filed on Jul. 21, 2011, now Pat. No. 8,761,493.

(60) Provisional application No. 61/825,658, filed on May 21, 2013.

(51) Int. Cl.
G06K 9/00 (2006.01)
G06T 7/00 (2006.01)
G06K 9/34 (2006.01)

(52) U.S. Cl.
CPC ............ *G06T 7/0012* (2013.01); *G06K 9/34* (2013.01); *G06T 7/0081* (2013.01); *G06T 7/0083* (2013.01); *G06T 7/0089* (2013.01); *G06T 2207/10081* (2013.01); *G06T 2207/20096* (2013.01); *G06T 2207/30036* (2013.01)

(58) Field of Classification Search
None
See application file for complete search history.

(56) References Cited

U.S. PATENT DOCUMENTS 5,431,562 A 7/1995 Andreiko et al.
6,210,162 B1 4/2001 Chishti et al.
(Continued)

FOREIGN PATENT DOCUMENTS

DE 10 2008 046 859 A1 4/2009
WO WO 2008/092009 7/2008
WO 2009/095837 A2 8/2009

OTHER PUBLICATIONS

Krsek et al., "Teeth and jaw 3D reconstruction in stomatology", *Proceedings of the International Conference on Medical Information Visualisation—BioMedical Visualisation*, 6 pages, 2007.
(Continued)

*Primary Examiner* — Atiba O Fitzpatrick

(57) ABSTRACT

A method of automatic tooth segmentation, the method executed at least in part on a computer system acquires volume image data for either or both upper and lower jaw regions of a patient and identifies image content for a specified jaw from the acquired volume image data. For the specified jaw, the method estimates average tooth height for teeth within the specified jaw, finds a jaw arch region, detects one or more separation curves between teeth in the jaw arch region, defines an individual tooth sub volume according to the estimated average tooth height and the detected separation curves, segments at least one tooth from within the defined sub-volume, and displays the at least one segmented tooth.

9 Claims, 27 Drawing Sheets

(56) References Cited

U.S. PATENT DOCUMENTS

| | | |
|---|---|---|
| 6,409,504 B1 | 6/2002 | Jones et al. |
| 7,317,819 B2 | 1/2008 | Janes |
| 7,324,661 B2 | 1/2008 | Kemp et al. |
| 7,460,709 B2 | 12/2008 | Grady |
| 8,244,017 B2 | 8/2012 | Chun et al. |
| 8,253,778 B2 | 8/2012 | Atsushi |
| 8,594,428 B2 | 11/2013 | Aharoni et al. |
| 8,605,973 B2 | 12/2013 | Wang et al. |
| 8,761,493 B2 | 6/2014 | Chen et al. |
| 2003/0039389 A1 | 2/2003 | Jones et al. |
| 2004/0175671 A1 | 9/2004 | Jones et al. |
| 2004/0227750 A1 | 11/2004 | Su et al. |
| 2006/0029275 A1 | 2/2006 | Li et al. |
| 2006/0147872 A1 | 7/2006 | Andreiko |
| 2006/0227131 A1 | 10/2006 | Schiwietz et al. |
| 2007/0127801 A1 | 6/2007 | Kalke |
| 2008/0030497 A1 | 2/2008 | Hu et al. |
| 2008/0118143 A1 | 5/2008 | Gordon et al. |
| 2008/0136820 A1 | 6/2008 | Yang et al. |
| 2008/0232539 A1 | 9/2008 | Pasini et al. |
| 2008/0310716 A1 | 12/2008 | Jolly et al. |
| 2009/0003672 A1 | 1/2009 | Maier et al. |
| 2009/0097727 A1 | 4/2009 | Jolly et al. |
| 2010/0278299 A1 | 11/2010 | Loustauneau et al. |
| 2011/0137626 A1 | 6/2011 | Matov et al. |
| 2012/0313941 A1 | 12/2012 | Li et al. |

OTHER PUBLICATIONS

Shah et al. "Automatic tooth segmentation using active contour without edges", 2006, IEEE Biometrics Symposium, 6 pages.

Akhoondali et al., "Rapid Automatic Segmentation and Visualization of Teeth in CT-Scan Data", *Journal of Applied Sciences*, pp. 2031-2044, 2009.

Gao et al., "Automatic Tooth Region Separation for Dental CT Images", *Proceedings of the 2008 Third International Conference on Convergence and Hybrid Information Technology*, pp. 897-901, (2008).

M Sadeghi, G. Tien, G. Hamarneh, M.S. Atkins, "Hands-free Interactive Image Segmentation Using Eyegaze", SPIE Medical Imaging 2009, vol. 7260, pp. 72601H1-72601H10.

Marie-Pierre Jolly, Leo Grady, "3D general lesion segmentation in CT", ISBI 2008, pp. 796-799.

Vladimir Vezhnevets, and Vadim Konouchine ,"GrowCut—Interactive Multi-Label N-D Image Segmentation by Cellular Automata,", *Int'l. Conf. Computer Graphics and Vision 2005*, 7 pages.

Hong Chen, et al., "Tooth Contour Extraction for Matching Dental Radiographs," Pattern Recognition, 2004 ICPR 2004 Proceedings of the 17th International Conference, 4 pages.

T.K. Schleyer, et al., "A Preliminary Analysis of the Dental Informatics Literature," Adv Dent Res, 17, pp. 20-24, Dec. 2003.

S.Y.Lee, et al., "Development of a Digital Panoramic X-ray Imaging System for Dental Applications," 2007 IEEE Nuclear Science Symposium Conference Record, vol. 4, pp. 2987-2990.

International Search Report mailed Oct. 30, 2012, International Application No. PCT/US2012/047265, 11 Pages.

R.L. Graham, "An Efficient Algorithm for Determining the Convex Hull of a Finite Planar Set", Jan. 28, 1972, Information Processing Letters 1 (1972) pp. 132-133, North-Holland Publishing Company.

International Search Report mailed Jan. 30, 2013, International Application No. PCT/US2012/047268, 3 Pages.

Sinop et al., "A Seeded Image Segmentation Framework Unifying Graph Cuts and Random Walker which Yields a New Algorithm," ICCV, 2007, pp. 1-8.

Supplementary European Search Report, Application No. EP12814726, dated Apr. 7, 2015, 2 pages.

Supplementary European Search Report, Application No. EP12814627, dated Mar. 20, 2015, 2 pages.

Xue Bai et al., Geodesic Matting: A Framework for Fast Interactive Image and Video Segmentation and Matting, International Journal of Computer Vision, vol. 8s, No. 2, DOI: 10.1007/s11263-008-1091-z, Apr. 2009, pp. 113-132.

Sh. Keyhaninejad et al., Automated Segmentation of Teeth In Multislice CT Images, International Conference On Visual Information Engineering, XP008082767, Jan. 2006, pp. 339-344.

T. Kondo et al., Robust Arch Detection and Tooth Segmentation in 3D Images of Dental Plaster Models, Medical Imaging and Augmented Reality, 2001 Proceedings International Workshop, XP010547535, ISBN: 978-0-7695-1113-9, pp. 241-246, Jun. 2010.

Mohammad Hosntalab et al., Segmentation of teeth in CT volumetric dataset by panoramic projection and variational level set, International Journal of Computer Assisted Radiology and Surgery, vol. 3, No. 3-4, Jun. 2008, pp. 257-265, XP055176492, ISSN: 1861-6410.

G.R.J. Swennen et al., A cone-beam CT based technique to augment the 3D virtual skull model with a detailed dental surface, International Journal of Oral and Maxillofacial Surgery, pp. 48-57, XP025986760, ISSN: 0901-5027, Jan. 2009.

Hui Gao et al., Individual tooth segmentation from CT images using level set method with shape and intensity prior, Pattern Recognition, Jul. 2010, pp. 2406-2417, XP026986849, ISSN: 0031-3203.

H. Akhoondali et al., Fully Automatic Extraction of Panoramic Dental Images from CT-Scan Volumetric Data of the Head, Journal of Applied Sciences, Jan. 2009, pp. 2106-2114, XP055110372.

1102

METHOD FOR TEETH SEGMENTATION AND ALIGNMENT DETECTION IN CBCT VOLUME

CROSS REFERENCE TO RELATED APPLICATIONS

This application claims the benefit of U.S. Provisional Patent Application Ser. No. 61/825,658 entitled "METHOD FOR TEETH SEGMENTATION AND ALIGNMENT DETECTION IN CBCT VOLUME" filed on May 21, 2013 in the names of Shoupu Chen et al., the contents of which are incorporated fully herein by reference.

This application is a Continuation-in-Part of U.S. Ser. No. 13/448,466 filed on Apr. 17, 2012 entitled "METHOD FOR TOOTH DISSECTION IN CBCT VOLUME" to Chen, which published as US 2013/0022254; which is itself a Continuation-in-Part of U.S. Ser. No. 13/187,596 filed on Jul. 21, 2011 entitled "METHOD AND SYSTEM FOR TOOTH SEGMENTATION IN DENTAL IMAGES" to Chen et al.

FIELD OF THE INVENTION

The present invention relates generally to image processing in x-ray computed tomography and, in particular, to automatic tooth segmentation, teeth alignment detection, and manipulation in a digital CBCT volume.

BACKGROUND OF THE INVENTION

Schleyer et al. ("A Preliminary analysis of the dental informatics literature", *Adv. Dent Res* 17:20-24), indicates a rise in the number of dental informatics papers in journals such as *Journal of the American Medical Informatics Association*, the *Journal of the American Dental Association*, and the *Journal of Dental Education*. Among topics surveyed, imaging, image processing, and computer-aided diagnosis were areas of interest.

Tooth image segmentation is of benefit for dental applications such as computer aided design, diagnosis, and surgery. Various approaches have been proposed in recent years to address tooth segmentation. However, researchers have noted the difficulty of tooth segmentation. For example, researchers Shah et al. describe a method for automating identification of deceased individuals based on dental characteristics in comparing post-mortem images with tooth images in multiple digitized dental records ("Automatic tooth segmentation using active contour without edges", 2006, *Biometrics Symposium*). Other methods are described by Krsek et al. in "Teeth and jaw 3D reconstruction in stomatology" (*Proceedings of the International Conference on Medical Information Visualisation—BioMedical Visualisation*, pp 23-28, 2007); Akhoondali et al. in "Rapid Automatic Segmentation and Visualization of Teeth in CT-Scan Data", *Journal of Applied Sciences*, pp 2031-2044, (2009); and Gao et al. in "Tooth Region Separation for Dental CT Images", *Proceedings of the 2008 Third International Conference on Convergence and Hybrid Information Technology*, pp 897-901, (2008).

In orthodontia applications, apparatus, system, and methods have been developed to facilitate teeth movement utilizing clear and removable teeth aligners as an alternative to braces. A mold of the patient's bite is initially taken and desired ending positions for the patient's teeth are determined, based on a prescription provided by an orthodontist or dentist. Corrective paths between the initial positions of the teeth and their desired ending positions are then planned. Aligners formed to move the teeth to the various positions along the corrective path are then manufactured.

US 2011/0137626 by Matov et al. describes a method to construct an arch form with the 3-dimensional (3-D) data of patient's teeth and facial axis points for the teeth. However, the Matov et al. method does not provide the ability to visualize maneuvering the teeth individually and digitally for treatment planning. With this and other methods, the digital data obtained from the Cone-Beam Computed Tomography (CBCT) dental volume image is not associated with desired teeth movement or a corresponding treatment strategy. This limits the usefulness of the volume image data.

Thus, there is a need for a system and method for automatically segmenting teeth from CBCT data, with tools for automatically analyzing tooth alignment and allowing a user to manipulate teeth digitally.

SUMMARY OF THE INVENTION

It is an object of the present invention to advance the art of tooth segmentation and analysis from cone beam CT (CBCT) images. A feature of the present invention is auto-segmentation of teeth without operator intervention. According to an embodiment of the present invention, an automated assessment of tooth alignment is provided, along with a display of alignment information.

These and other aspects, objects, features and advantages of the present invention will be more clearly understood and appreciated from a review of the following detailed description of the preferred embodiments and appended claims, and by reference to the accompanying drawings.

According to an aspect of the present invention, there is provided a method of automatic tooth segmentation, the method executed at least in part on a computer and comprising: acquiring volume image data for either or both upper and lower jaw regions of a patient; identifying image content for a specified jaw from the acquired volume image data and, for the specified jaw: (i) estimating average tooth height for teeth within the specified jaw; (ii) finding a jaw arch region; (iii) detecting one or more separation curves between teeth in the jaw arch region; (iv) defining an individual tooth sub volume according to the estimated average tooth height and the detected separation curves; (v) segmenting at least one tooth from within the defined sub-volume; and displaying the at least one segmented tooth.

BRIEF DESCRIPTION OF THE DRAWINGS

The foregoing and other objects, features, and advantages of the invention will be apparent from the following more particular description of the embodiments of the invention, as illustrated in the accompanying drawings, in which.

DETAILED DESCRIPTION OF THE INVENTION

Figure 1:
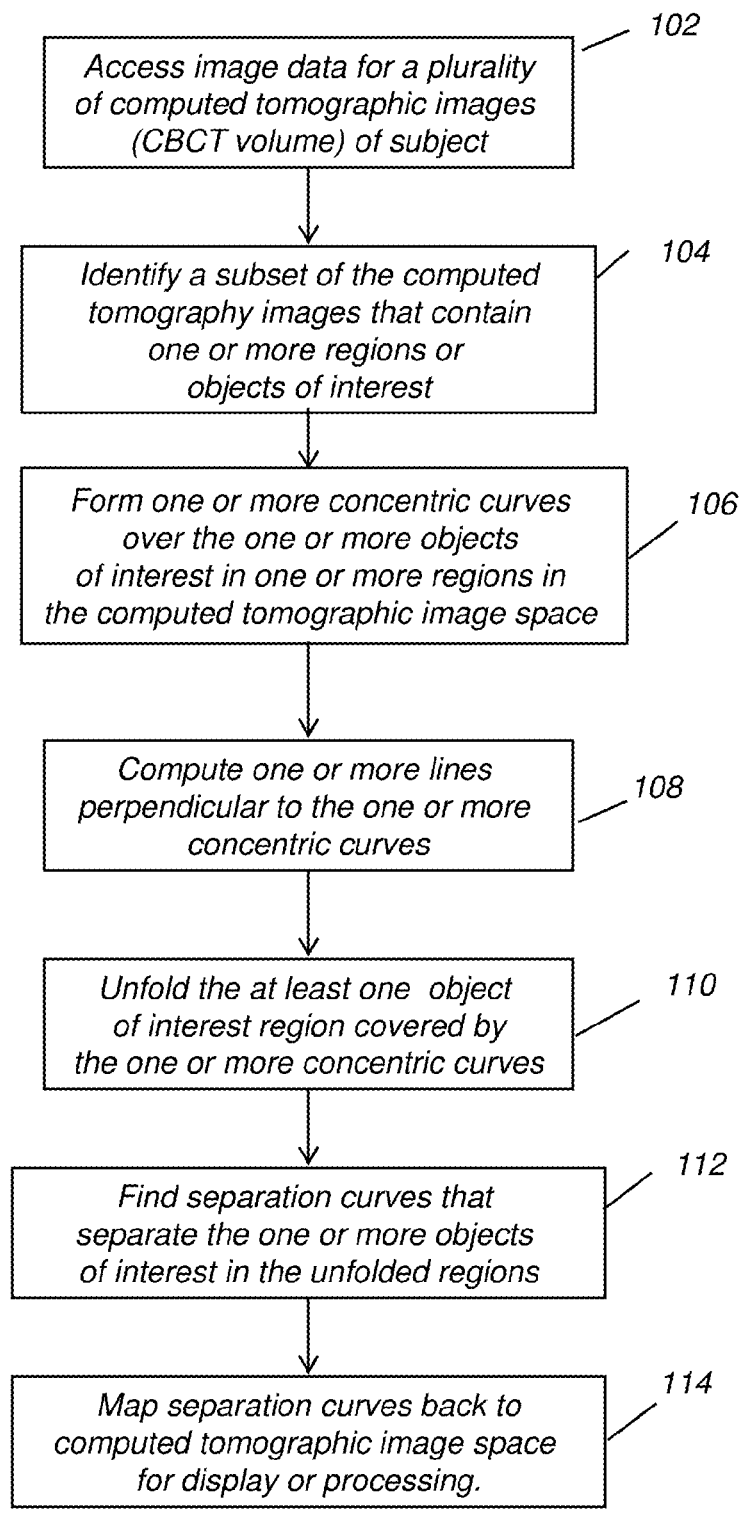
FIG. 1 is a logic flow diagram showing processes for forming one or more separation curves according to an embodiment of the present invention.

In the following detailed description of embodiments of the present invention, reference is made to the drawings in which the same reference numerals are assigned to identical elements in successive figures. It should be noted that these figures are provided to illustrate overall functions and relationships according to embodiments of the present invention and are not provided with intent to represent actual size or scale.

Where they are used, the terms "first", "second", "third", and so on, do not necessarily denote any ordinal or priority relation, but may be used for more clearly distinguishing one element or time interval from another.

In the context of the present disclosure, the term "image" refers to multi-dimensional image data that is composed of discrete image elements. For 2D (two-dimensional) images, the discrete image elements are picture elements, or pixels. For 3D (three-dimensional) images, the discrete image elements are volume image elements, or voxels.

In the context of the present disclosure, the term "code value" refers to the value that is associated with each volume image data element or voxel in the reconstructed 3D volume image. The code values for CT images are often, but not always, expressed in Hounsfield units.

In the context of the present disclosure, the term "geometric primitive" relates to an open or closed geometric figure or shape such as a triangle, rectangle, polygon, circle, ellipse, free-form shape, line, traced curve, or other traced pattern.

The term "highlighting" for a displayed feature has its conventional meaning as is understood to those skilled in the information and image display arts. In general, highlighting uses some form of localized display enhancement to attract the attention of the viewer. Highlighting a portion of an image, such as an individual organ, bone, or structure, or a path from one chamber to the next, for example, can be achieved in any of a number of ways, including, but not limited to, annotating, displaying a nearby or overlaying symbol, outlining or tracing, display in a different color or at a markedly different intensity or gray scale value than other image or information content, blinking or animation of a portion of a display, or display at higher sharpness or contrast.

In the context of the present disclosure, the descriptive term "high density object" generally indicates a mass, or object such as a tooth, that exceeds the density of the surrounding materials (such as soft tissues or air) and would be identified in a radiographic image as a high density object by a skilled practitioner. Because of differences related to dosage, however, it is impractical to specify any type of absolute threshold for defining high density.

The term "set", as used herein, refers to a non-empty set, as the concept of a collection of elements or members of a set is widely understood in elementary mathematics. The term "subset", unless otherwise explicitly stated, is used herein to refer to a non-empty proper subset, that is, to a subset of the larger set, having one or more members. For a set S, a subset may comprise the complete set S. A "proper subset" of set S, however, is strictly contained in set S and excludes at least one member of set S.

In the context of the present disclosure, the term "dissection" relates to methods used for separating one object from another, adjacent object. Thus, dissection of a subject tooth in an intraoral volume image defines a boundary between the subject tooth and an adjacent or neighboring tooth.

In the context of the present disclosure, the terms "viewer", "operator", and "user" are considered to be equivalent and refer to the viewing practitioner or other person who views and manipulates an image, such as a dental image, on a display monitor. An "operator instruction" or "viewer instruction" is obtained from explicit commands entered by the viewer, such as using a computer mouse or touch screen or keyboard entry.

The subject matter of the present invention relates to digital image processing and computer vision technologies, which is understood to mean technologies that digitally process data from a digital image to recognize and thereby assign useful meaning to human-understandable objects, attributes or conditions, and then to utilize the results obtained in further processing of the digital image.

Image segmentation is a process that partitions a digital image into a defined set of features so that image analysis can be simplified. Segmentation assigns a label to each image pixel so that pixels that have the same label are considered to be a part of the same structure or type of feature and can share common treatment. Due to factors such as the relative complexity of the image content and difficulties presented by the shape and structure of teeth, conventional attempts at tooth segmentation have not been sufficiently robust for widespread application.

A number of known image segmentation methods familiar to those skilled in the image analysis arts, such as region growing, utilize "seeds". Seeds are pixels that are either identified automatically from the image content or explicitly identified by a user. As the name implies, the seed is used as a hint or starting point for a region growing process. In region growing, a region of the image is defined from its initial seed pixel(s) or voxels (s) by successively analyzing neighboring pixel (or voxel) values relative to the seed pixel(s) and incorporating a pixel (or voxel) into a region when its difference from the seed pixel (or voxel) is below a predetermined value.

Akhoondali et al. proposed an automatic method for the segmentation and visualization of teeth in multi-slice CT-scan data of the head in "Rapid Automatic Segmentation and Visualization of Teeth in CT-Scan Data", *Journal of Applied Sciences*, pp 2031-2044, (2009). The algorithm that was employed consists of five main procedures. In the first part, the mandible and maxilla are separated using maximum intensity projection in the y direction and a step like region separation algorithm. In the second part, the dental region is separated using maximum intensity projection in the z direction, thresholding and cropping. In the third part, the teeth are rapidly segmented using a region growing algorithm based on four thresholds used to distinguish between seed points, teeth and non-tooth tissue. In the fourth part, the results are visualized using iso-surface extraction and surface and volume rendering. A semi-automatic method is also proposed for rapid metal artifact removal. However, in practice, it is very difficult to select a total of five different threshold values for a proper segmentation operation. Their published results show relatively poor dissection between the teeth in some cases.

Gao et al. disclosed a method to construct and visualize the individual tooth model from CT image sequences for dental diagnosis and treatment (see "Tooth Region Separation for Dental CT Images", *Proceedings of the* 2008 *Third International Conference on Convergence and Hybrid Information Technology*, pp 897-901, 2008). Gao's method attempts to separate teeth for CT images where the teeth touch each other in some slices. The method finds the individual region for each tooth and separates two teeth if they touch. Their proposed method is based on distinguishing features of the oral cavity structure. The use of full 3D data, instead of 2D projections, may cause loss of some information. The described method initially separates upper and lower tooth regions and then fits the dental arch using fourth order polynomial curves, after a series of morphological operations. The method assumes that there exists a plane separating two adjacent teeth in 3D space. In this plane, the integral intensity value reaches a minimum. Along each arch point, this method obtains a plane and calculates the integral intensity. These values are then used to draw a profile. After analyzing all the local minima, this method obtains the separating point and the position of the separating plane. The information for the tooth region can guide the segmentation of both the individual tooth contours in 2D space and the tooth surfaces in 3D space. However, it appears that Gao's method may not actually separate (or dissect) the teeth correctly; the separation (or dissection) curves that are obtained in many cases cut through the teeth region of interest in certain slices.

Referring to the logic flow diagram of FIG. 1, there is shown a sequence of steps used for teeth dissection for a dental CBCT volume (accessed in an image access step 102) in one embodiment. A volume contains image data for one or more images (or equivalently, slices). An original reconstructed CT volume is formed using standard reconstruction algorithms using multiple 2D projections or sinograms obtained from a CT scanner. Normally, only a fraction or subset of the images that form the volume contain high density objects and is selected for processing; the rest of the CT reconstructed volume accurately represents soft tissue or air.

This selection of a subset of images for this procedure is done in an image selection step 104. A number of neighboring high density objects in an image (or slice) forms a region. A number of neighboring high density objects in another image (or slice) forms another region.

Figure 2:
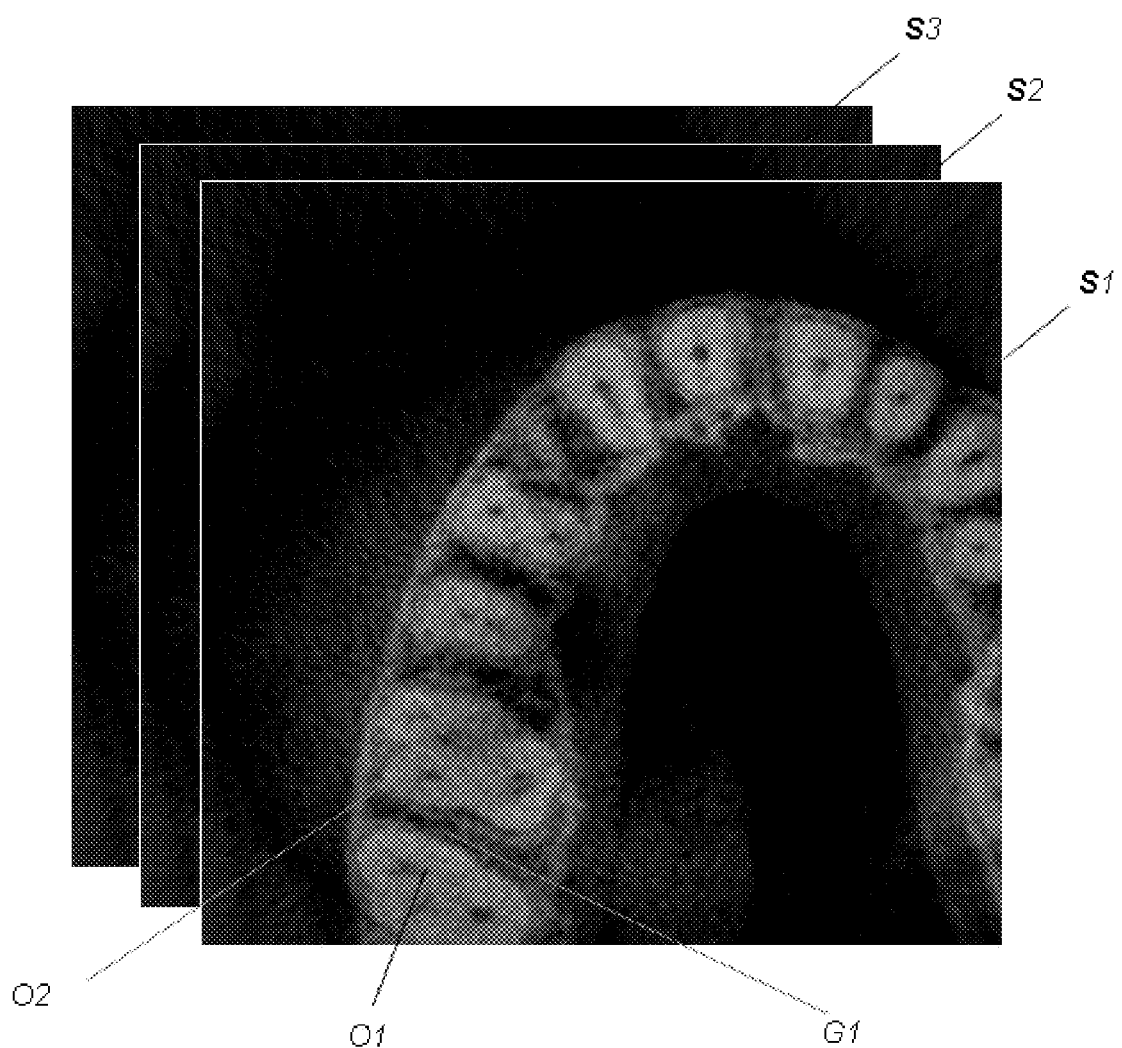
FIG. 2 is a view of a set of reconstructed CBCT images having objects of interest.

FIG. 2 shows an exemplary dental CBCT volume that contains three image slices S1, S2, and S3. High density object examples are objects O1 and O2 shown in slice S1; these are parts of two adjacent or neighboring teeth. High density objects including objects O1 and O2 in S1 constitute a region in S1. Similarly, high density objects like O1 and O2 in S2 constitute a region in S2. The same applies to S3.

There is a gap G1 between objects O1 and O2 in S1. The method of the present invention provides ways to identify a separation curve that passes through gap G1, optionally following initial user input and conditions, including identification of appropriate regions, as described subsequently.

Figure 3A:
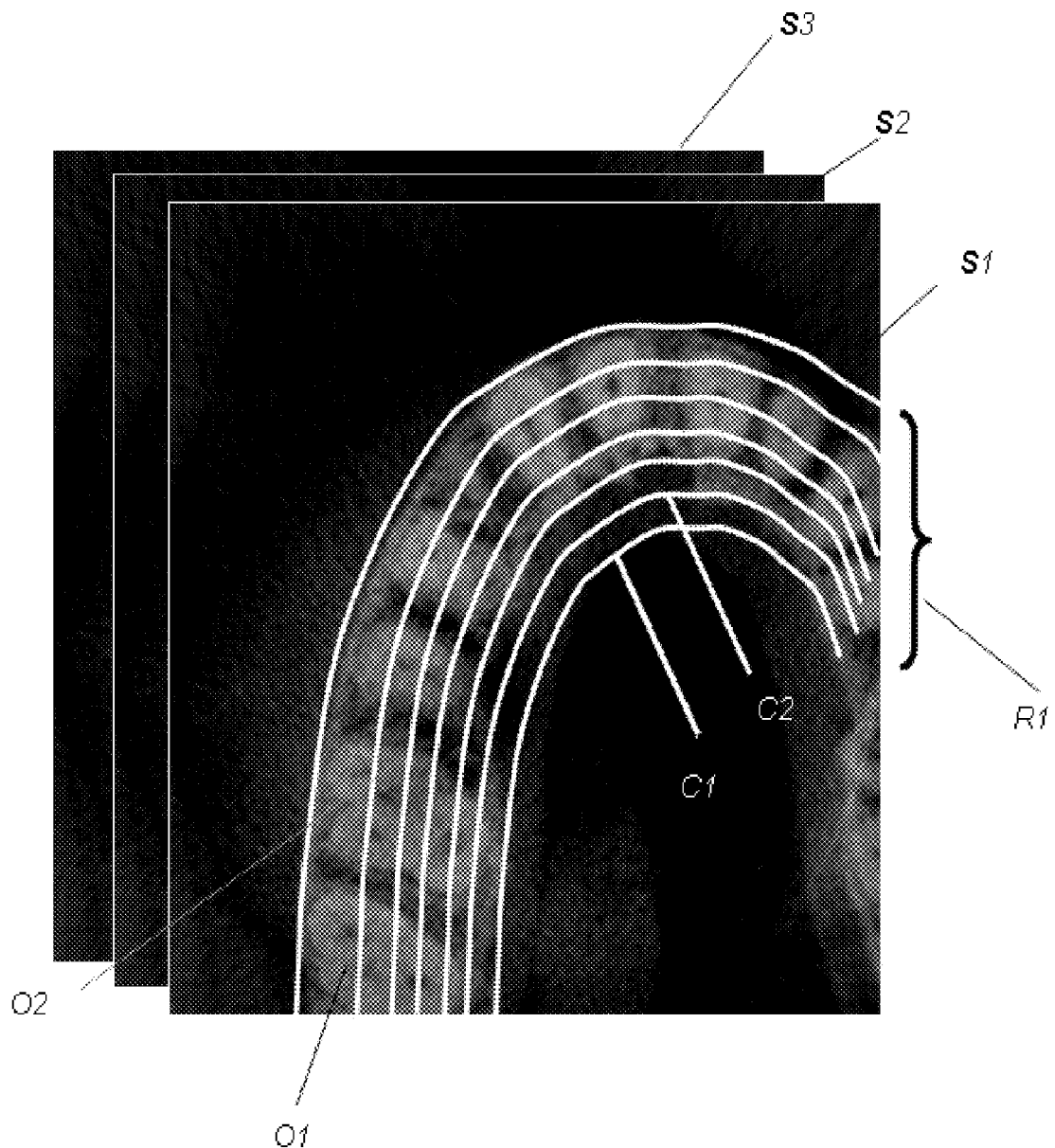
FIG. 3A is a view of a set of reconstructed CBCT images having features of interest with concentric curves overlaid.

In slice S1, the high density objects (teeth in this case) are collectively arranged in a geometric arch shape that can be decomposed into a set of concentric curves. FIG. 3A shows an exemplary set of concentric curves including curves C1 and C2 in slice S1. The requirement for forming a set of concentric curves is that these curves should cover (enclose) the region that is formed from the high density objects. An exemplary region R1 is shown in S1, encompassing the teeth in this slice. Similarly, a corresponding arch-shaped region, with corresponding curves, is formed for the region that contains teeth in image slices S2 or S3.

Therefore, in a curve-forming step 106 of the FIG. 1 sequence, concentric curves are formed over the at least one object of interest. These curves are used for generating teeth separation curves for separating teeth in the subsequent steps. Using these concentric curves in slice S1 and in corresponding regions in slices S2, S3, and other slices, a curved slab can be formed as a stack of these regions. The curved slab can then be cropped from the image volume for further processing.

Figure 3B:
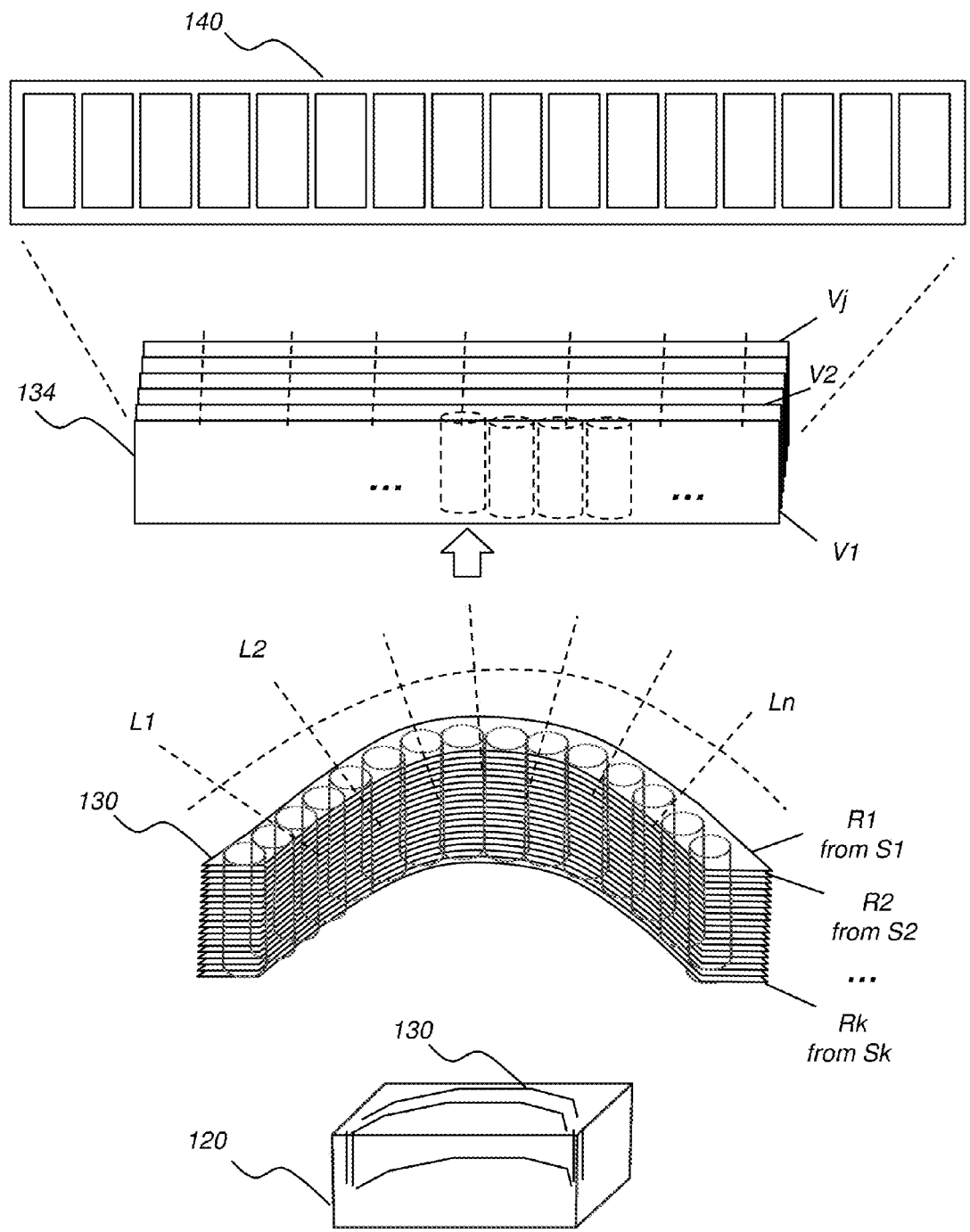
FIG. 3B is a schematic diagram that shows how a panoramic image is formed by unfolding a curved sub-volume.

As shown schematically in FIG. 3B, by stacking the regions that are defined along these concentric curves, that is, stacking of region R1 from slice S1 in FIG. 3A and corresponding regions R2, . . . Rk from slices S2, . . . Sk that would be defined in the same way, a curved slab can be formed as a curved sub-volume 130, containing one or more of the features of interest; here, the features of interest are regions of one or more high density objects cropped from the larger image volume.

The diagram of FIG. 3B shows schematically how the segmentation sequence of the present invention proceeds to generate one or more panoramic views 140 from a dental CT volume 120. A first set of operations, through step 106 in FIG. 1, generates the curved slab of curved sub-volume 130, from the original CT volume 120. An unfold line computation step 108 then provides a utility that will be used subsequently for unfolding the curved sub-volume 130 along a selected curve to generate the desired flattened or unfolded panoramic view 140. In its effect, this maps the leaf of the foliation back to a plane, which can be readily manipulated and viewed as an image. As the sequence shown in FIG. 3B indicates, the curved sub-volume 130 is formed by stacking slices aligned generally along a first direction. Unfolding then operates in a planar direction that is orthogonal to this first direction, as shown in the view of an unfolded slab, termed an unfolded sub-volume 134. For unfolding, image data elements that lie along or nearby each fold line are re-aligned according to a realignment of the fold lines. This realignment generally aligns the fold lines from their generally radial arrangement to a substantially parallel orientation. Image data elements that were initially aligned with the fold lines in the original, generally radial arrangement follow the fold line re-orientation, effectively "flattening" the curved sub-volume with little or no distortion of the tooth and its position relative to other teeth.

Unfolded sub-volume 134 can be visualized as a stacked series of vertical slice images V1, V2, ... Vj, as shown in FIG. 3B. Each vertical slice provides a panoramic image obtained at some depth within unfolded sub-volume 134. Subsequent steps then present the unfolded views to the user as a type of index to the volume that is to be assigned separation curves. That is, selection from the unfolded view enables the user to provide hint (or seed) information that is used for dissection or separation and, in most cases, subsequent segmentation of the tooth or other object.

The one or more concentric curves or curved paths in FIG. 3A could be traced using an automated approach or a semi-automatic approach. In an automated approach, slice S1 can be processed through a sequence of steps that include noise filtering, smoothing, intensity thresholding, binary morphological filtering, medial curve estimation, and pruning to identify a first curve that fits or approximates the arch shape of the teeth region. Subsequent concentric curves can then be defined using the shape and position of the first estimated curve as a starting point. These steps described are exemplary steps that are well known to those skilled in the art; other manual and automated processing steps could alternately be performed for providing a structure to support unfolding.

A semi-automatic approach can be simpler and more robust, without requiring an elaborate operator interface. For such an approach, user input initializes a few nodes along an imaginary medial axis of the arch shape region in slice S1 (FIG. 3A, 3B), for example. These few nodes then become starting points for a curve-fitting algorithm, such as a spline-fitting sequence, for example, to form a first curve that fits the arch shape of the teeth region. Subsequent concentric curves can then be generated using the first estimated curve. Steps for operator-assisted curve definition and generation of parallel or otherwise related curves are familiar to those skilled in the image analysis arts.

Once the concentric curves are formed in step 106 (FIG. 1), computation step 108 computes lines that are generally perpendicular to the concentric curves in the tomographic image space. These perpendicular lines facilitate finding separation curves between the teeth in subsequent processing. Exemplary perpendicular lines are shown as unfold lines L1 and L2 in FIG. 4. It is readily understood that two neighboring perpendicular lines could touch or intersect at one end but be spaced apart at the other end by examining the exemplary perpendicular lines in slice S1 in FIG. 4.

In an unfolding step 110 (FIG. 1) the curved slab containing one or more of the regions of one or more high density objects is unfolded with the help of the computed unfold lines that are perpendicular to the concentric curves.

Figure 4:
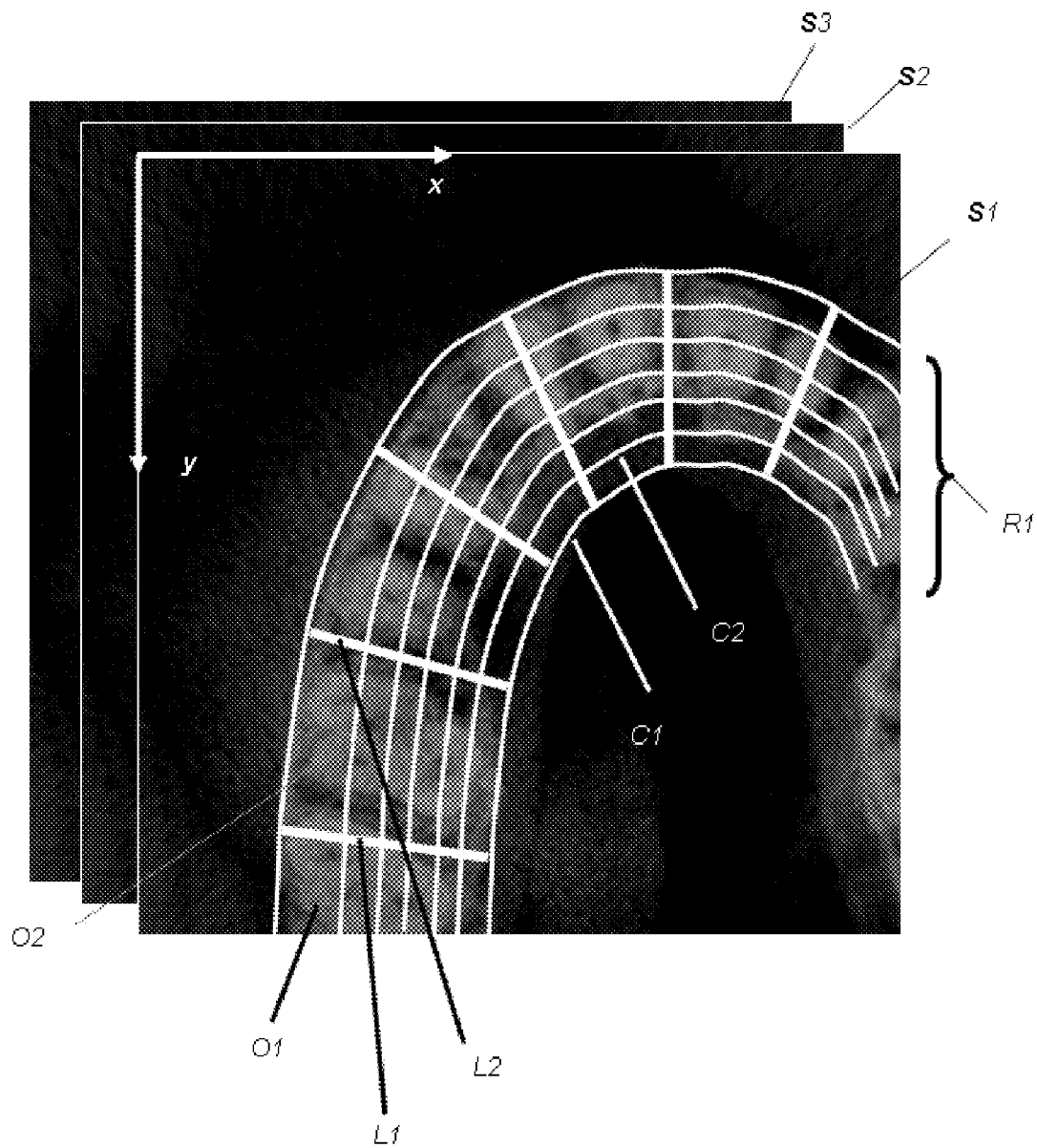
FIG. 4 is a view of a set of reconstructed CBCT images having objects of interest with concentric curves and lines for unfolding formed perpendicular to the concentric curves overlaid.
Figure 5A:
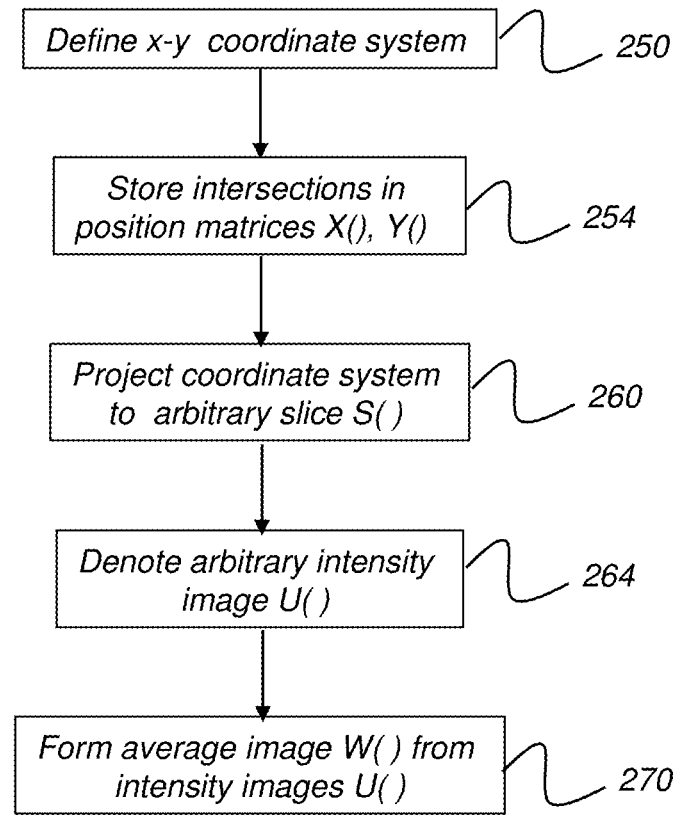
FIG. 5A is a logic flow diagram that shows a sequence of steps for forming an averaged image W from a number of intensity images.

The logic flow diagram of FIG. 5A shows the sequence for unfolding the curved slab according to an embodiment of the present invention. In a definition step 250, an x-y coordinate system for slice S1, as shown in FIG. 4, is defined. The origin is at the upper left corner of slice S1. Suppose there are a total of M concentric curves (C1, C2, ... Cm, ... CM), and a total of N perpendicular lines (L1, L2, ... Ln, ... LN). An x position matrix of size of M by N is denoted by X. A y position matrix of size of M by N is denoted by Y. A storage step 254 stores the x position of an intersection point of Cm and Ln at matrix X(m,n). The y position of an intersection point of Cm and Ln is stored at matrix Y(m,n). In a slice assignment step 260, an arbitrary slice S is denoted with the same x-y coordinate system defined in definition step 250 and shown in FIG. 4.

Continuing with the FIG. 5A sequence, in an intensity image step 264 an arbitrary intensity image by U of size of M by N is generated. Define: $U(m,n)=S(Y(m,n), X(m,n))$.

Therefore, for a specific slice, a series of intensity images are generated:

$$U1(m,n)=S1(Y(m,n),X(m,n))$$

$$U2(m,n)=S2(Y(m,n),X(m,n))$$

$$U3(m,n)=S3(Y(m,n),X(m,n)), \text{etc.}$$

Collectively, the intensity images U1, U2, U3, etc. formed in this way constitute an unfolded curved slab. Then, in an average image step 270 (FIG. 5A), having the unfolded curved slab ready, computing an averaged image W of the unfolded curved slab in the axial direction yields:

$$W=(U1+U2+U3+\ldots+UK)/K,$$

where K is the number of slices contained in the unfolded curved slab.

Figure 5B:
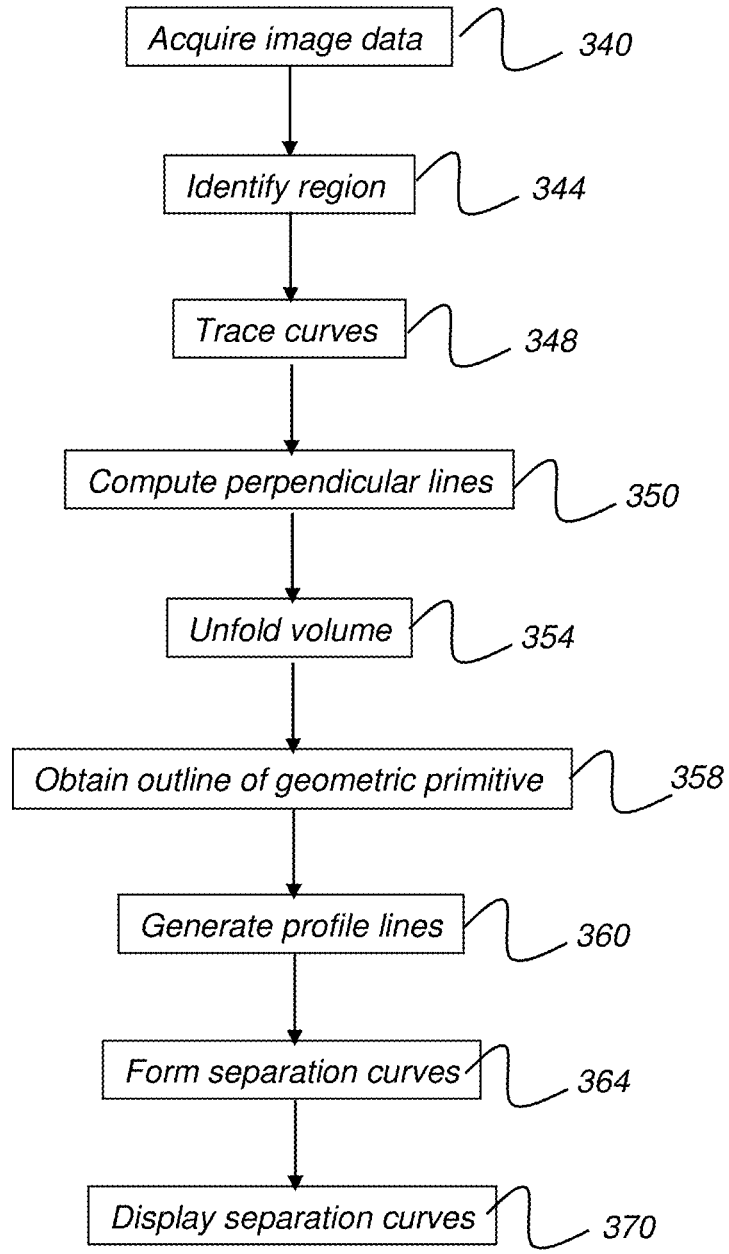
FIG. 5B is a logic flow diagram that shows a sequence of steps for generating and displaying a separation curve between a first and a second object in a volume image.
Figure 5C:
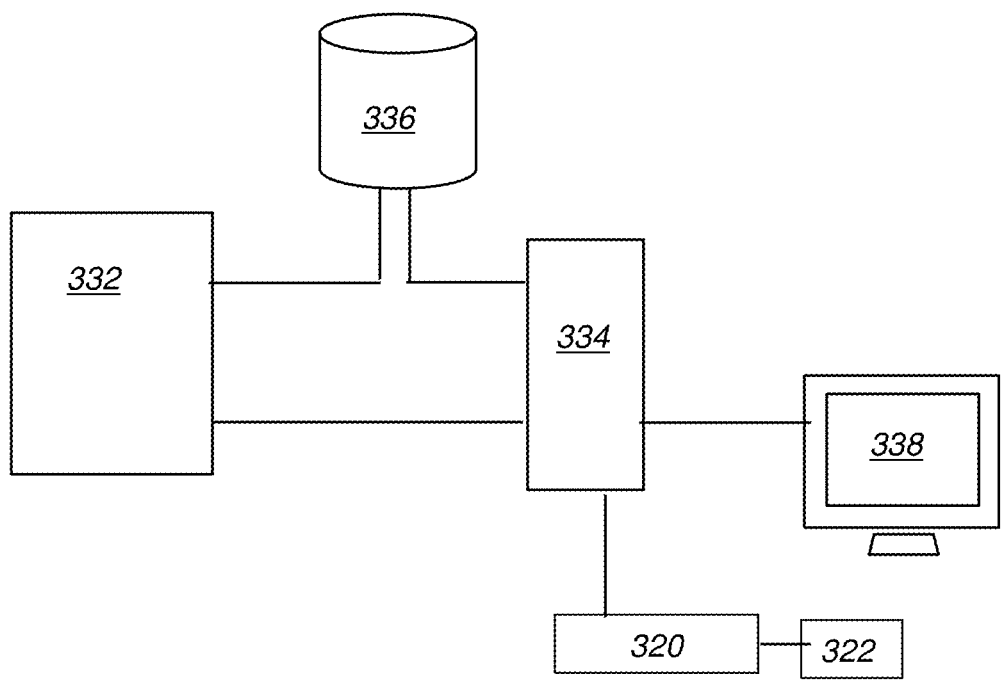
FIG. 5C shows an imaging apparatus that is used for forming one or more separation curves.

FIG. 5B is a logic flow diagram that shows a sequence of steps for generating and displaying a separation curve between a first and a second object, such as between two teeth, in a volume image. FIG. 5C shows an imaging apparatus 330 that is used for the steps shown in FIG. 5B. Imaging apparatus 330 has an image acquisition apparatus 332 such as a CBCT imaging system, for example, that provides the volume image of the patient. The volume image data may be obtained directly from image acquisition apparatus 332 or from a memory 336 or other storage system, such as a PACS (picture archiving and communication system) or other system that stores the acquired image data. Imaging apparatus 330 has a computer system or other logic processor 334 with a display console 338 that provides both display and operator interface functions, such as through a keyboard 320 and mouse 322 or incorporating a touch screen, for example. In an image acquisition step 340, the volume image data of the patient or other subject is acquired from memory 336 or other source.

Continuing with the FIG. 5B sequence, a region identification step 344 then identifies the region of the volume image that contains at least the first and second teeth or other objects. A curve tracing step 348 then forms one or more concentric curves over at least the first and second objects in the region according to the volume image data. A computation step 350 then computes one or more lines perpendicular to the one or more concentric curves. An unfolding step 354 unfolds the region covered by the one or more concentric curves to generate an unfolded view of the region. An obtain outline step 358 obtains an outline of a geometric primitive that is traced with respect to the first object in the unfolded region, based on operator input. Entry of a geometric primitive by the operator is described in more detail subsequently. A profile line generation step 360 then generates a plurality of profile lines across the first and second objects using information obtained from the outline of the geometric primitive that is obtained in step 358. Gap points in each profile line are then identified and joined together in a separation curve forming step 364. Separation curves are then displayed relative to the volume image in a display step 370.

Figure 6A:
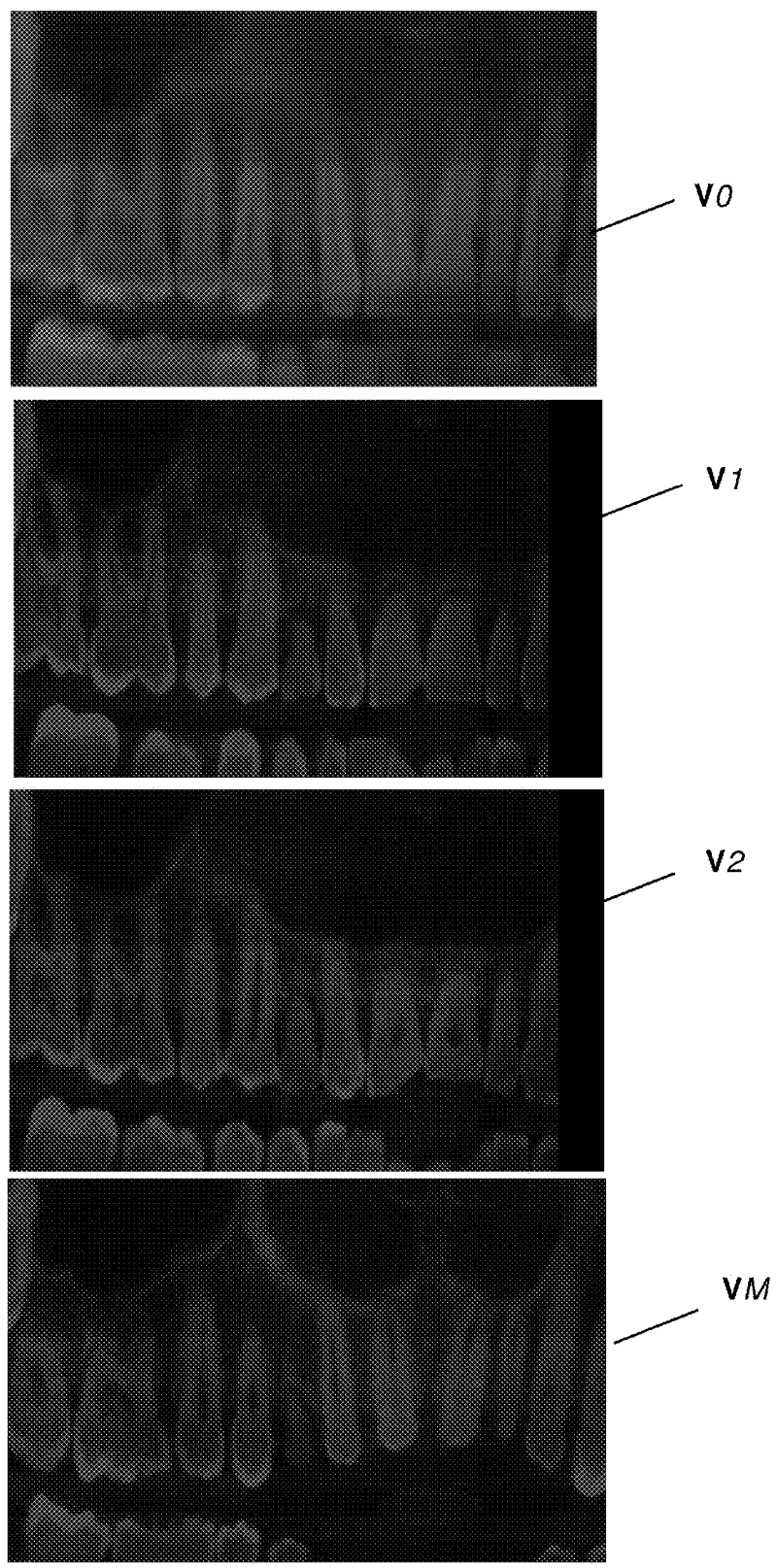
FIG. 6A shows different views of a volume image.

FIGS. 6A through 6D show various features of the process and show how the geometric primitive that is entered by the operator is used to provide starting points for tooth dissection. FIG. 6A shows views V0-VM for different unfolded views of the teeth. View V1 is the averaged view that is obtained using the data in each slice V1-VM. Slices V1, V2, and VM are individual coronal view slices, generated as was described earlier with reference to FIG. 3B. Although a geometric primitive can be traced onto any one or more of the individual slices of views V1-VM, it is generally preferable to have the operator trace a geometric primitive onto the averaged view V0. Although the operator can trace the geometric primitive onto any view of the unfolded volume image, the coronal view is advantaged for ease of visualization and usability.

Figure 6B:
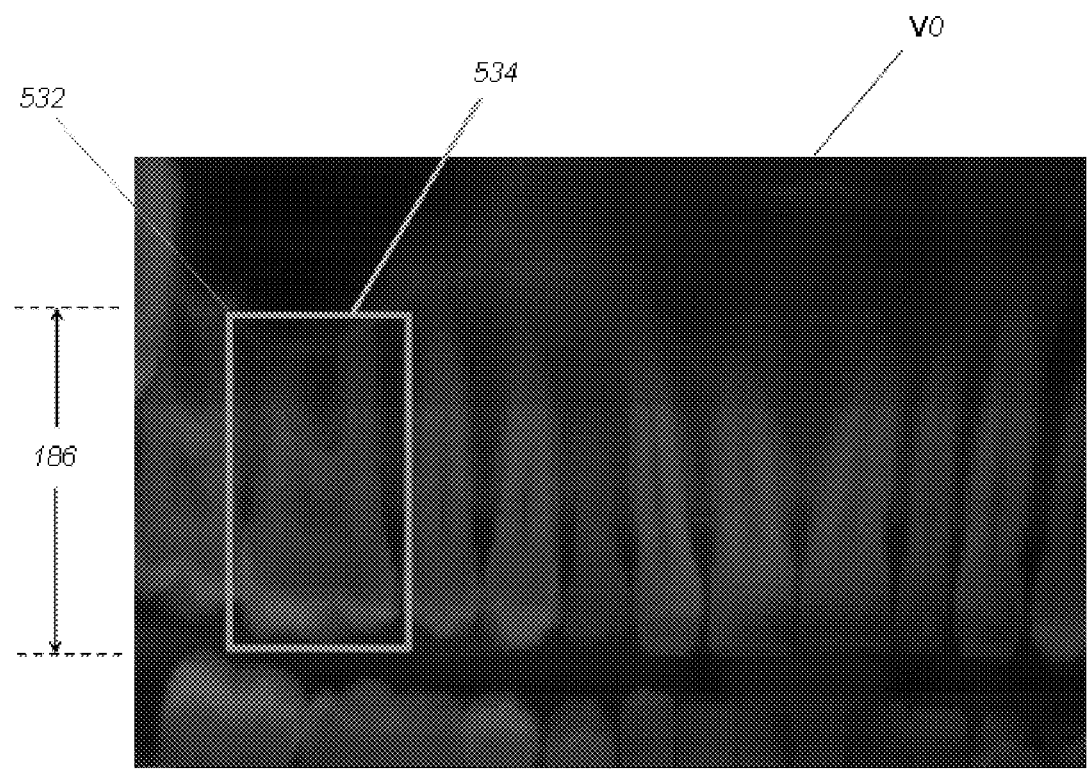
FIG. 6B shows a volume image with an outlined tooth, obtained from user interface input.

FIG. 6B shows operator entry of a box 532 as one type of geometric primitive 534 that helps to identify starting points for tooth dissection. Box 532 can be readily entered with a computer mouse in one action, using standard drag-and-hold procedure to define diagonal corners, for example. The geometric primitive that is entered defines a height 186 and edges for providing start points for dissection processing. The height that is defined helps to limit the amount of data that is processed in subsequent steps, so that volume image data outside of the region of the teeth or other objects can be ignored for this purpose. Alternate types of geometric primitive include points, lines, circles, or free-form closed or open figures or shapes, for example.

Figure 6C:
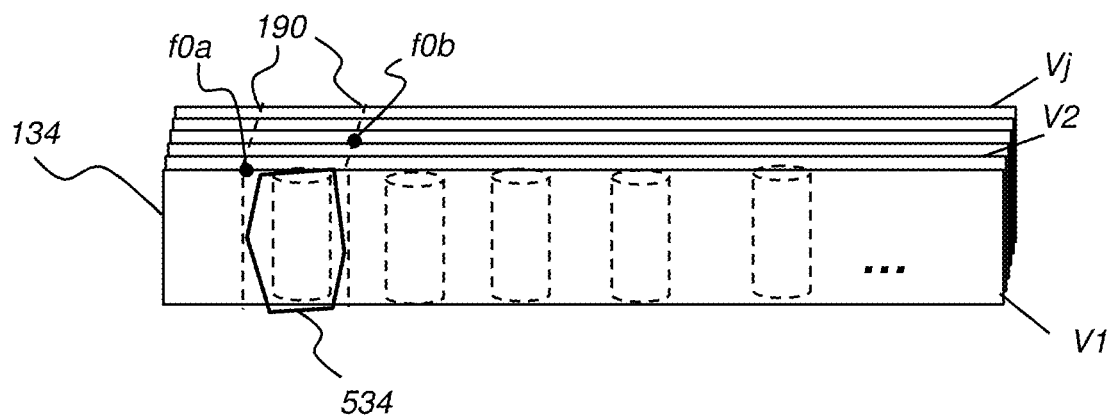
FIG. 6C is schematic diagram of a perspective view of vertical (coronal) slices.

The schematic diagram of FIG. 6C shows, from a perspective view of vertical (coronal) slices V1-Vj, how edges of the geometric primitive 534 are used. Extreme edges or sides of geometric primitive 534 are extended to define extended lines 190 that can be used to identify starting points f0a and f0b for each vertical slice V1-Vj. Starting point f0a is shown on the first slice V1; starting point f0b is shown in the middle of the stack of coronal slices. In practice, the starting points can be identified at any point along the extended line 190, that is, in reference to the designations shown in FIG. 6C, in the image data corresponding to any of vertical slices V1-Vj.

Figure 6D:
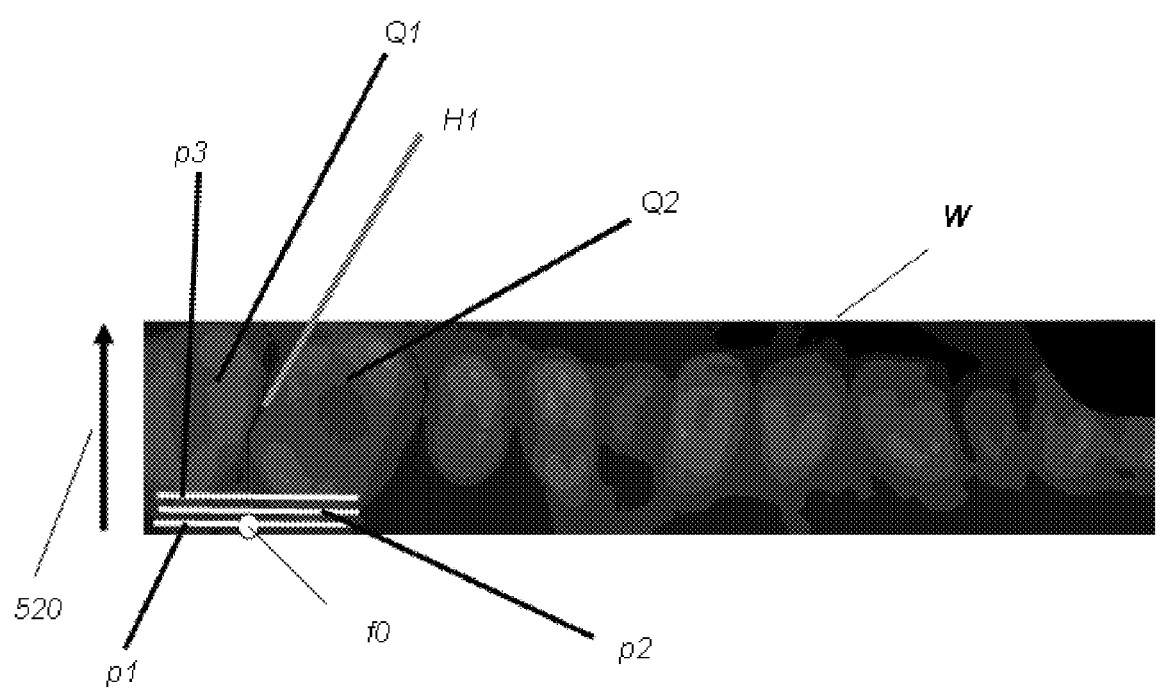
FIG. 6D is an image that shows the use of profile lines for analyzing the gap between teeth and generating a separation curve.

FIG. 6D shows an axial view averaged image W corresponding to the coronal view schematic of FIG. 6C. Image W has size M by N pixels. In unfolded FIG. 6D, the high density objects (teeth) are aligned approximately along a horizontal direction instead of along a curved medial axis as was shown in FIG. 2. Lines drawn in the horizontal direction correspond to the top edges of slices V1-Vj in FIG. 6C. Three representative profile lines p1, p2, and p3 are indicated for a number of the slices in this view.

The unfolding operation of the curved slab, as described earlier with reference to FIG. 3B, makes it possible to trace separation curves between the teeth in a more straightforward manner, as described in more detail later. Objects O1 and O2 in FIG. 2 correspond to objects Q1 and Q2 in FIG. 6D; the shape of either O1 or O2 may be transformed to Q1 and Q2 due to the unfolding operation. A gap G1 between O1 and O2 in FIG. 2 now appears as gap H1 in the unfolded view of FIG. 6D. Given these transformations, the task of automatically finding a separation curve that passes through gap G1, with or without an initial condition imposed by the user, then becomes the task of finding a separation curve that passes through gap H1. This task is then more easily accomplished by searching along the same direction indicated by an arrow 520 for each pair of teeth in image W in FIG. 6D.

With reference to the sequence of FIG. 1, identifying the separation curve between two teeth in image W is carried out in a curve identification step 112 by identifying points of minimum intensity, or valley points along profile lines. As noted with respect to FIGS. 6C and 6D, profile lines correspond to the top edges of each vertical slice (viewed along the top in the perspective view of FIG. 6C and from the top in the plan view of FIG. 6D.) A point of minimum intensity corresponds to an image element, voxel or pixel, at a position in the image data. The use of profile lines is a convenience and helps to visualize the direction in which processing progresses in order to identify the succession of valley points needed to define the separation curve.

Figure 7A:
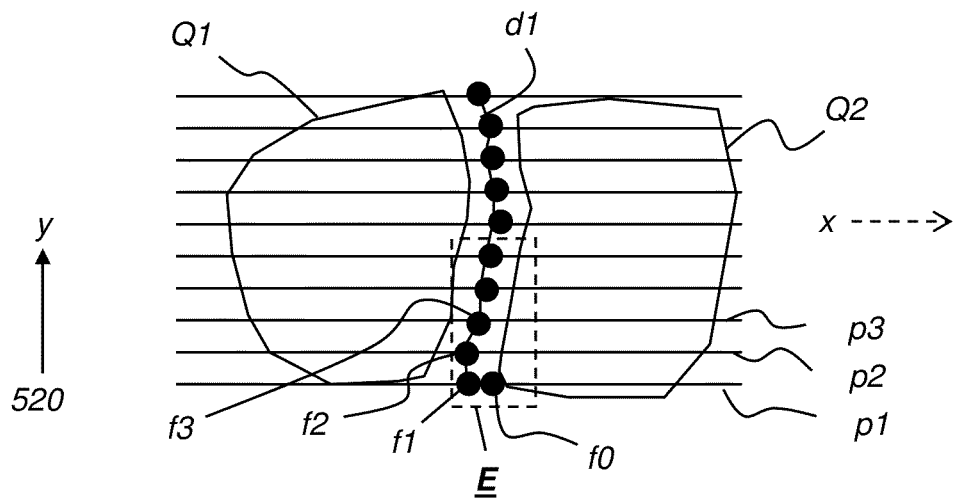
FIG. 7A is a plan view that shows how valley points are used to generate a separation curve.
Figure 7B:
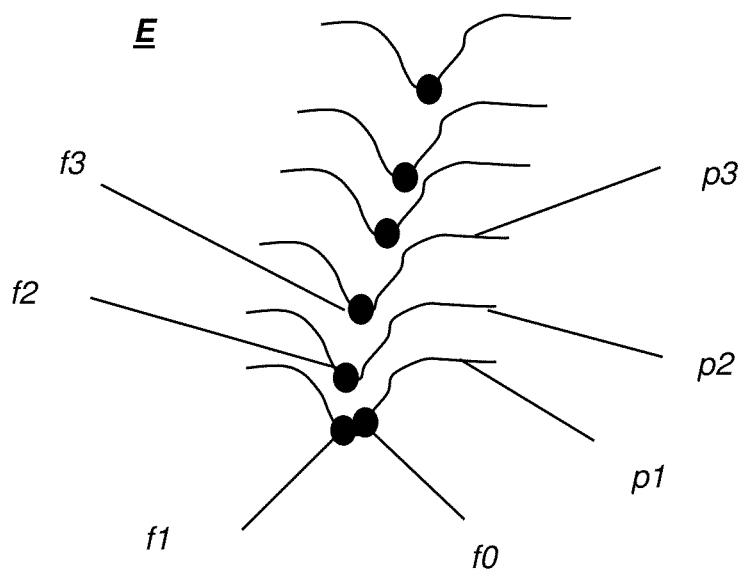
FIG. 7B is a schematic diagram in perspective, illustrating finding valleys on profile lines in the average image of an unfolded curved slab.

FIGS. 7A and 7B show, in schematic form, how the separation curve d1 between objects Q1 and Q2 is formed by connecting points in an incremental fashion. FIG. 7A is a plan view, showing multiple profile lines p1, p2, p3, and so on. FIG. 7B shows, from a perspective view, how profile lines within a section identified as inset E in FIG. 7A, provide valley points f1, f2, f3, and so on. An initial starting point f0 is identified from an edge of a geometric primitive traced by the operator, as was described earlier with reference to FIGS. 6B-6D. In the example shown, analysis of the image data along profile line p1 indicates that a nearby point f1 is a more suitable valley point and is thus substituted for f0 as the effective starting point for forming separation curve d1. Then, progressing from point f1 in the direction of arrow 520 (the y direction) and searching along the next profile line p2, the next valley point f2 is identified. According to an embodiment of the present invention, a constraint is imposed on how far the next valley point can be displaced in the +/−x-direction (orthogonal to arrow 520, as shown in FIG. 7A) with each step in the y direction. This constraint is in the x direction that is substantially orthogonal to the path of the separation curve at any valley point. According to an exemplary embodiment of the present invention, in moving in the y direction from one profile line to the next, the x-coordinate of the next valley point must be within +/−6 voxels (or pixels) of the x-coordinate for the preceding valley point that has been identified. It can be appreciated that this constraint value helps to prevent abrupt changes in the overall direction of the separation curve and can be adjusted appropriately for controlling the path of the separation curve.

The same process repeats until all the profile lines pn are searched. The collection of valley points including f1, f2 and f3 are connected to form a separation curve d1 that separates teeth Q1 and Q2 or other adjacent objects. In the same manner, a separation curve on the other side of a tooth is similarly generated. The process repeats as often as needed until all needed pairs of teeth are equipped with separation curves.

Figure 8:
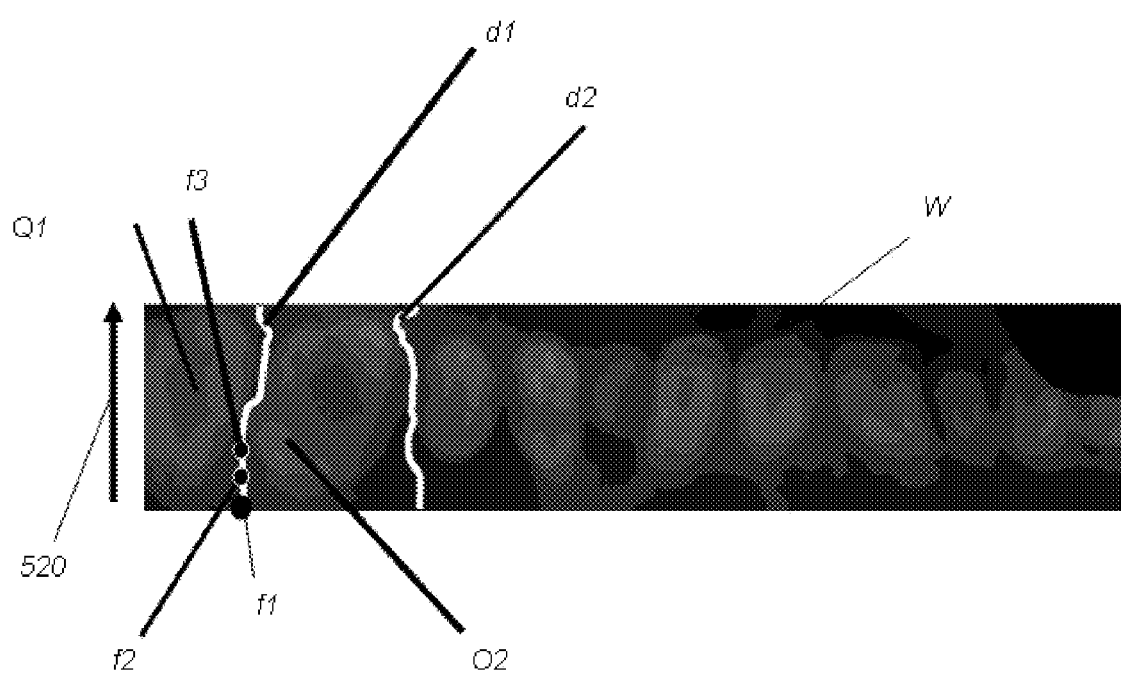
FIG. 8 is an average image of an unfolded curved slab with the identified separation curves overlaid.
Figure 9:
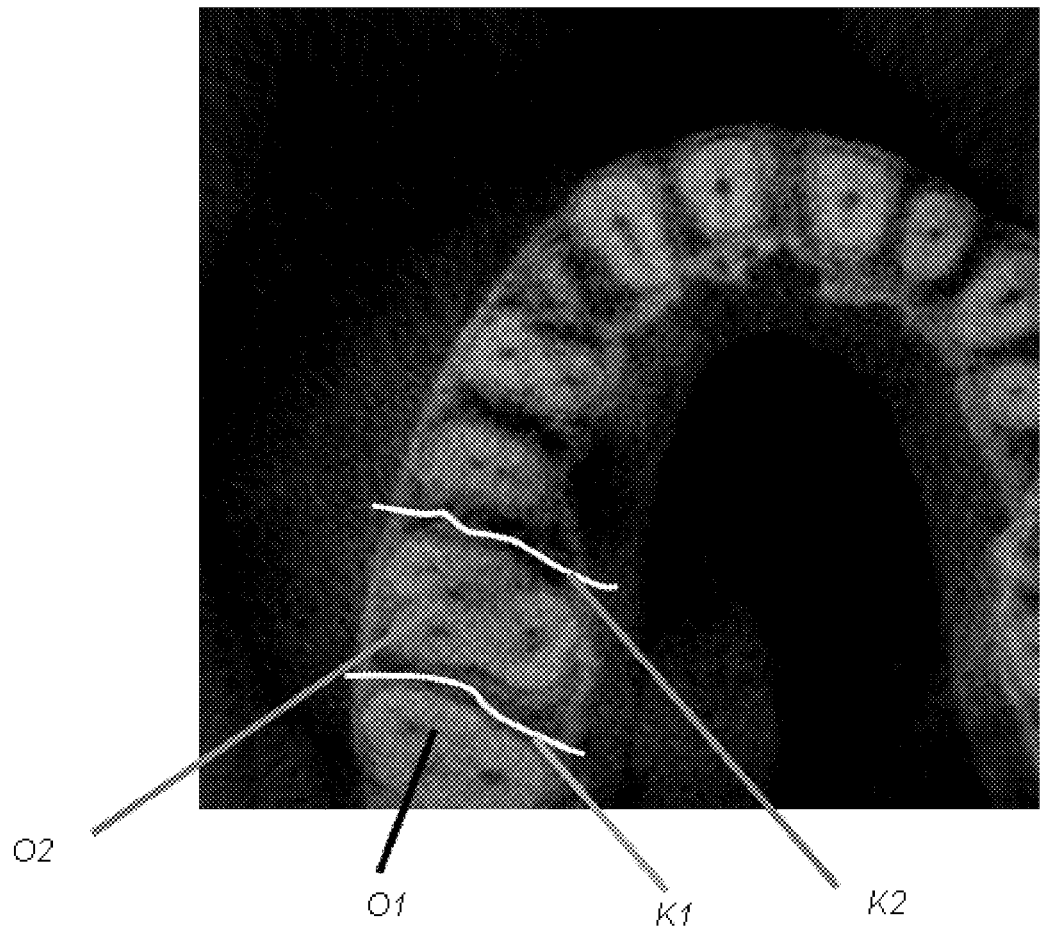
FIG. 9 is a view of a reconstructed CBCT image having separation curves mapped between the objects of interest.

Then, referring back to FIG. 1, a mapping step 114 maps the separation curves back to the computed tomographic image space as shown in FIGS. 8 and 9. FIG. 8 is the unfolded view of averaged image W. FIG. 9 is a view of a reconstructed CBCT volume image having separation curves K1 and K2 mapped between the objects of interest. Recalling the definitions of X(m,n) and Y(m,n) that are stated previously, a vector (m,n) can be readily mapped to (Y(m,n), X(m,n)) in the computed tomographic image space. A pair of separation curves d1 and d2 in FIG. 8 correspond to curves K1 and K2 in FIG. 9. These mapped separation curves can then be displayed on a control monitor associated with the computer logic processor or other processor that executes the procedures described herein. Separation curves can be displayed in a 2D or 3D rendering of the associated image data. In a volume rendering, a separation curve can be viewed from any suitable angle.

Figure 10:
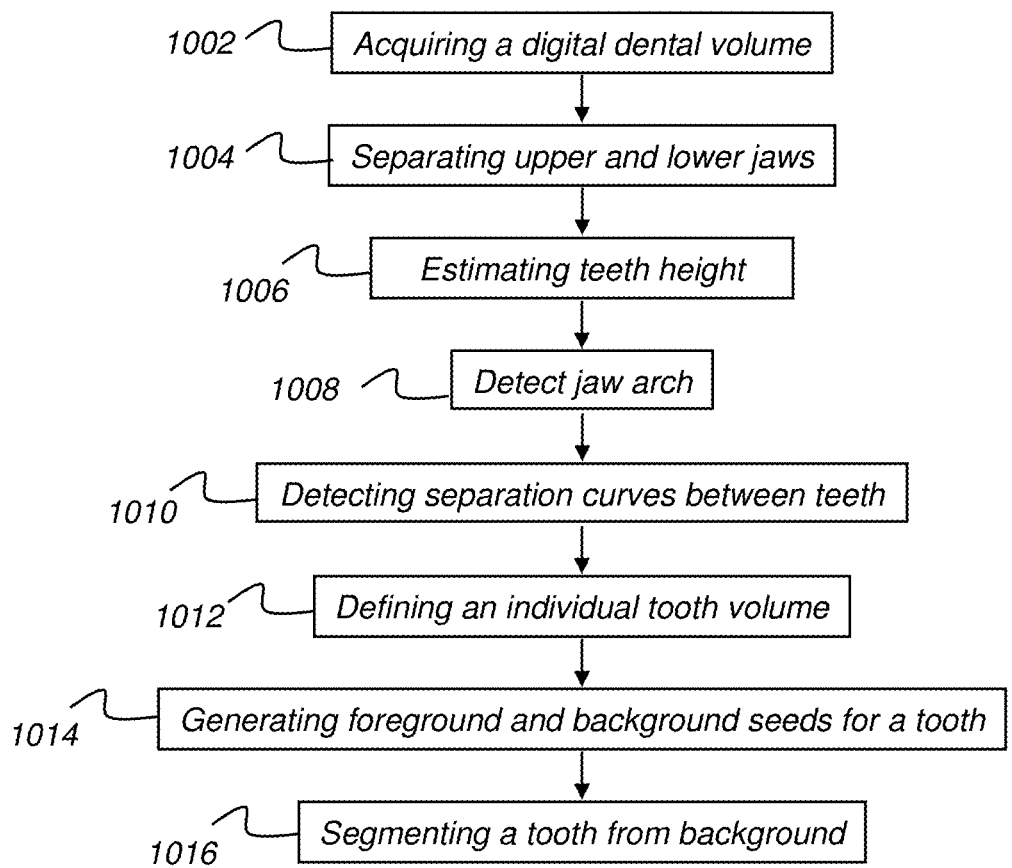
FIG. 10 is a logic flow diagram that describes an auto-segmentation sequence according to an embodiment of the present invention.

Now referring to FIG. 10, there is shown a logic flow diagram that describes an auto-segmentation sequence according to an embodiment of the present invention. A digital dental volume such as a CBCT volume is acquired in a data acquisition step 1002. The upper teeth (jaw) and lower teeth (jaw) are the regions of particular interest. In general, teeth have higher code values than most of the other tissues and bones in a CBCT volume. An adaptive thresholding approach, for example, can quickly isolate the upper and lower regions from the rest of the image content. Adaptive thresholding is an approach for analyzing and segregating image content that is familiar to those skilled in image processing. With this initial processing, the next step is to separate upper and lower jaws in a jaw separation step 1004.

The boundary of separation between the upper and lower jaws is readily detected by evaluating the code value profile in the sagittal or coronal views of the jaw regions, or in a panoramic view, such as the unfolded view shown in FIG. 6B and generated as described earlier with reference to FIG. 3B. For instance, in FIG. 6B, the lower code values in that portion of an image between the upper teeth and lower teeth provide a good indication of separation between the upper jaw and the lower jaw. Accumulated information from lower code values for successive image slices or, alternately, for a portion of the volume image content, facilitates the task of identifying and differentiating upper and lower jaws in the volume image.

Figure 11A:
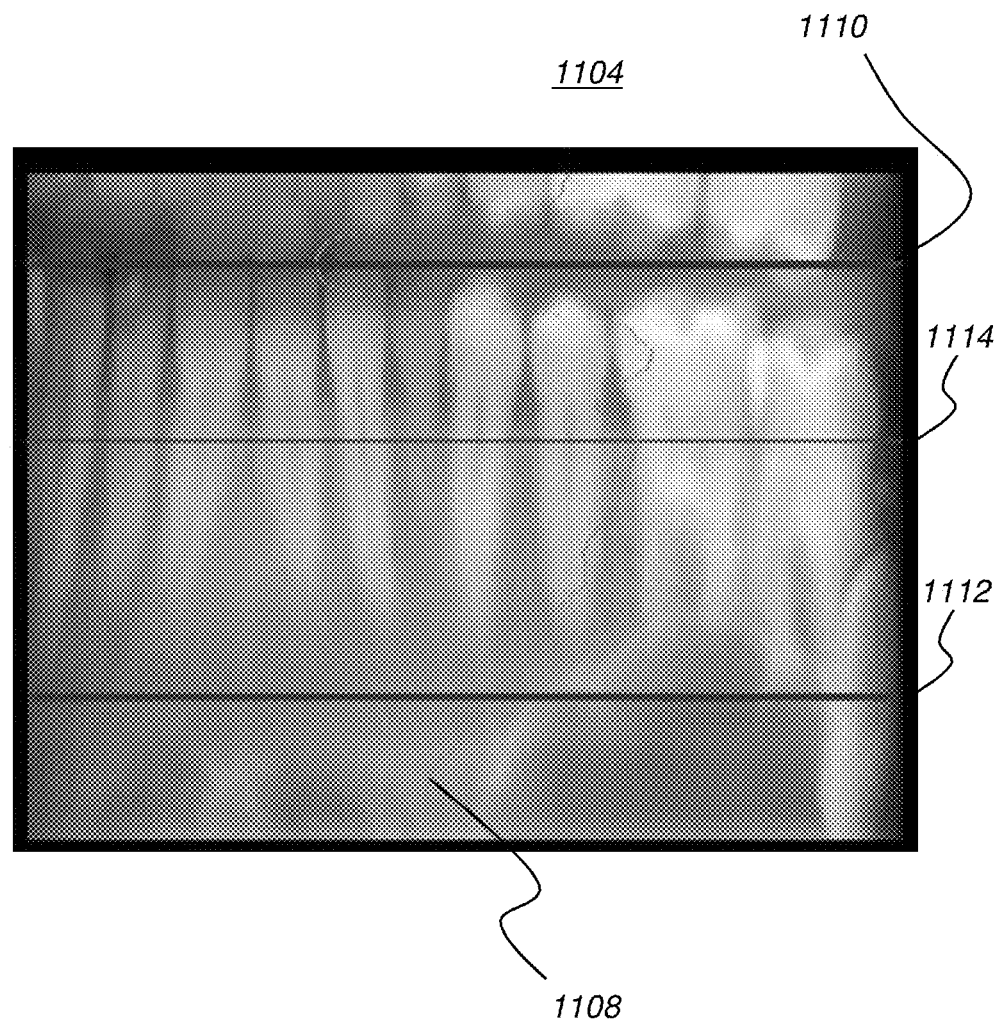
FIG. 11A is a 2-D image that shows how average height is computed from the image content.

After separating the upper and lower jaws, the sequence of FIG. 10 next estimates the average teeth height for the upper teeth and lower teeth respectively in an estimation step 1006. A simple and quick approach employed in the present invention is, for each tooth in the upper jaw or lower jaw, to project all the teeth voxels to a single line, then evaluate the projection profile. For instance, referring to the unfolded view of FIG. 11A, generated as described earlier with reference to FIG. 3B, projecting the lower teeth voxels either from left to right or from right to left in an image 1104 generates a line profile 1108 which, in turn, shows the length of the teeth projected onto the line. A line 1110 indicates a low point in line profile 1108 that indicates the gap between lower and upper teeth. A second line 1112 indicates a relative low line marking the base of the teeth. The distance between lines 1110 and 1112 yields a length that indicates the average height for upper teeth or lower teeth. An optional line 1114 indicates the approximate location of the gumline; the distance between lines 1114 and 1110 indicates approximate height of the crown. The average height is used subsequently to define a bounding cube for a tooth volume.

Figure 11B:
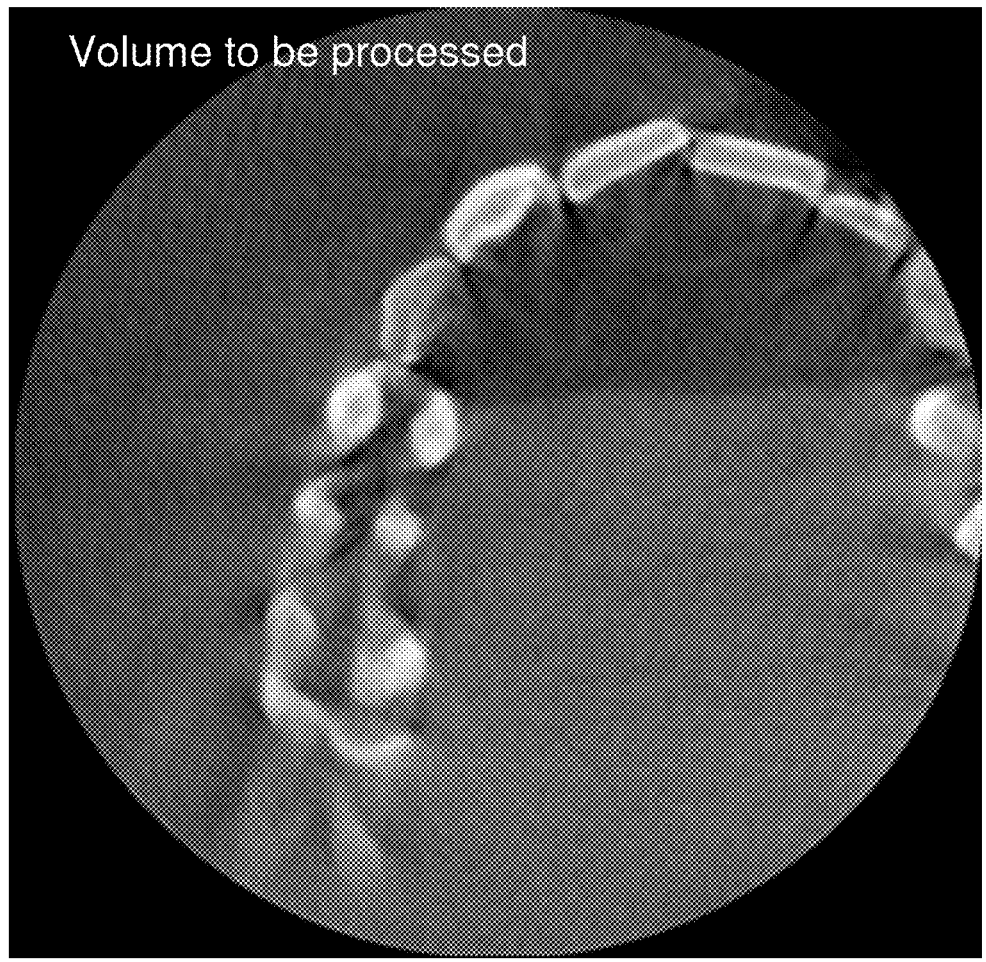
FIG. 11B shows a volume image to be processed.
Figure 12:
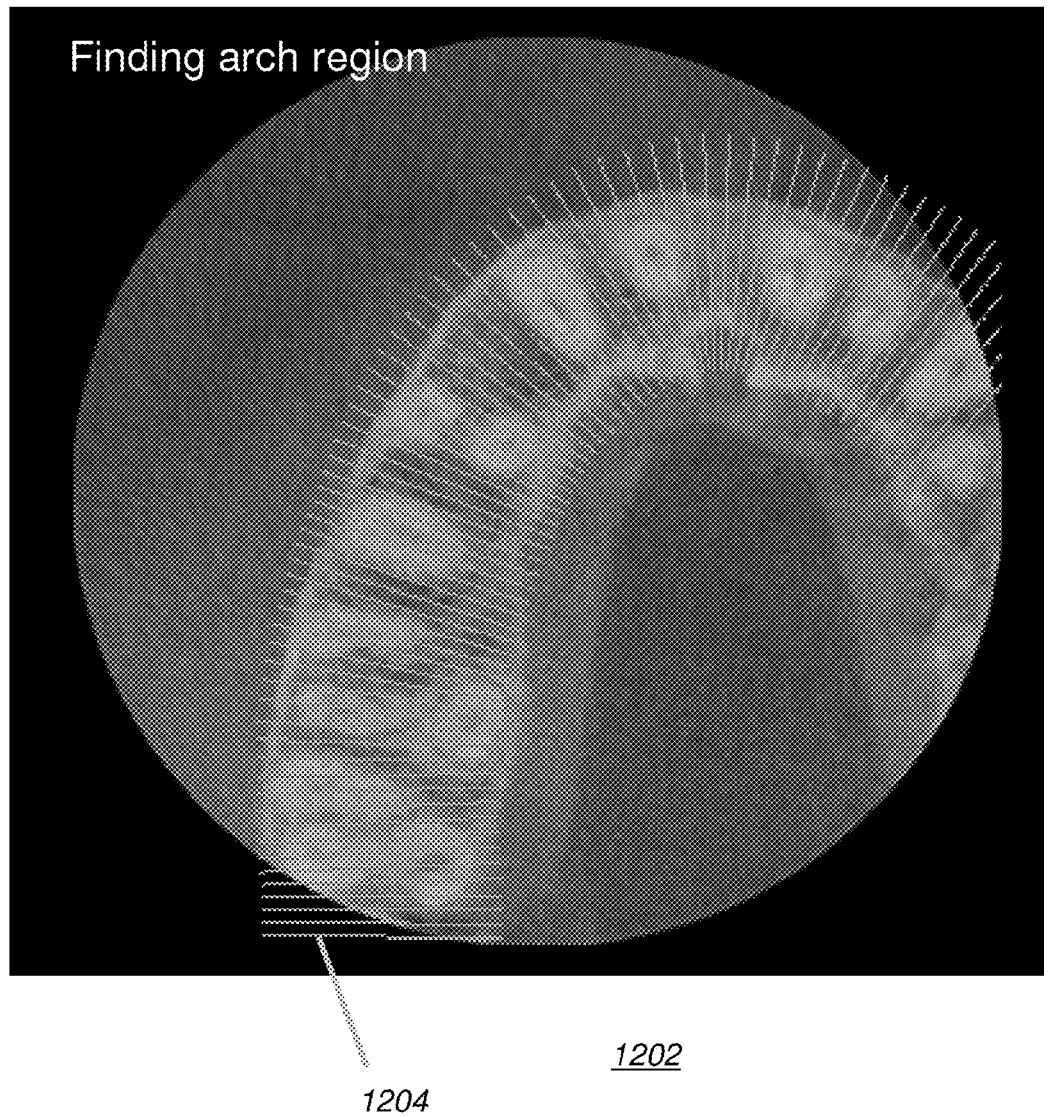
FIG. 12 shows the image of FIG. 11B with the arch region identified.

A jaw arch detection step 1008 in the FIG. 10 sequence performs similar tasks to those performed for unfolding a region in steps 106 through 110 (FIG. 1), and then proceeds to detect the jaw arch region for a volume, such as for a volume image 1102 represented in FIG. 11B. Results of step 1008 are shown in the example of an image 1202 in FIG. 12, where lines 1204 indicate the detected jaw arch region.

A line identification and mapping step 1010 in FIG. 10 performs similar tasks to that of steps 112 and 114 in FIG. 1, finding the dissection or separation curve between the teeth. It should be noted that the separation curve is often generally linear, but may have some number of angled or curvilinear segments. Unlike the FIG. 1 procedure, however, in step 1010, the initial starting point f0 is not identified from an edge of a geometric primitive traced by the operator; instead, the initial start point f0 is detected automatically by the software. A search routine searches for the valley points (locally lowest code values) on the medial line of the jaw arch region. These valley points can be used as the initial start point f0s.

The purpose of finding the separation curves is to adequately define a bounding cube as a sub-volume for an individual tooth within the volume image. In order for a bounding cube to completely enclose a tooth, the separation curve that is initially identified is shifted a few voxels in position away from a bounded region. For example, in FIG. 13, an image 1302 is shown. For Tooth A, one of the original dissection or separation curves is a curvilinear line 1304, the other separation curve (separating Tooth A and Tooth B) is a curvilinear line 1306. For the bounding cube boundary for Tooth B, the separation curve that is used (separating Tooth B and Tooth A) is a curvilinear line 1308, shifted outward from the original curvilinear line 1306.

Figure 13:
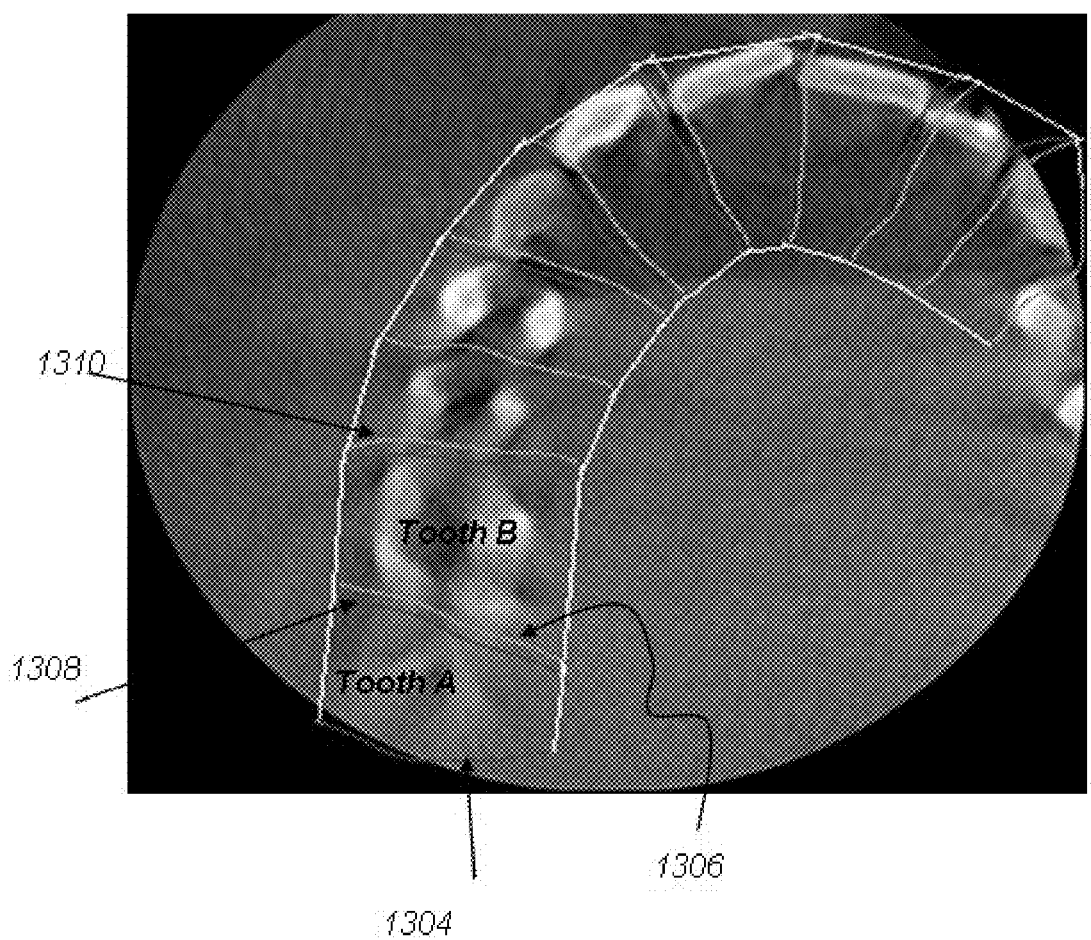
FIG. 13 shows the image of FIG. 11B with separation curves identified.
Figure 14:
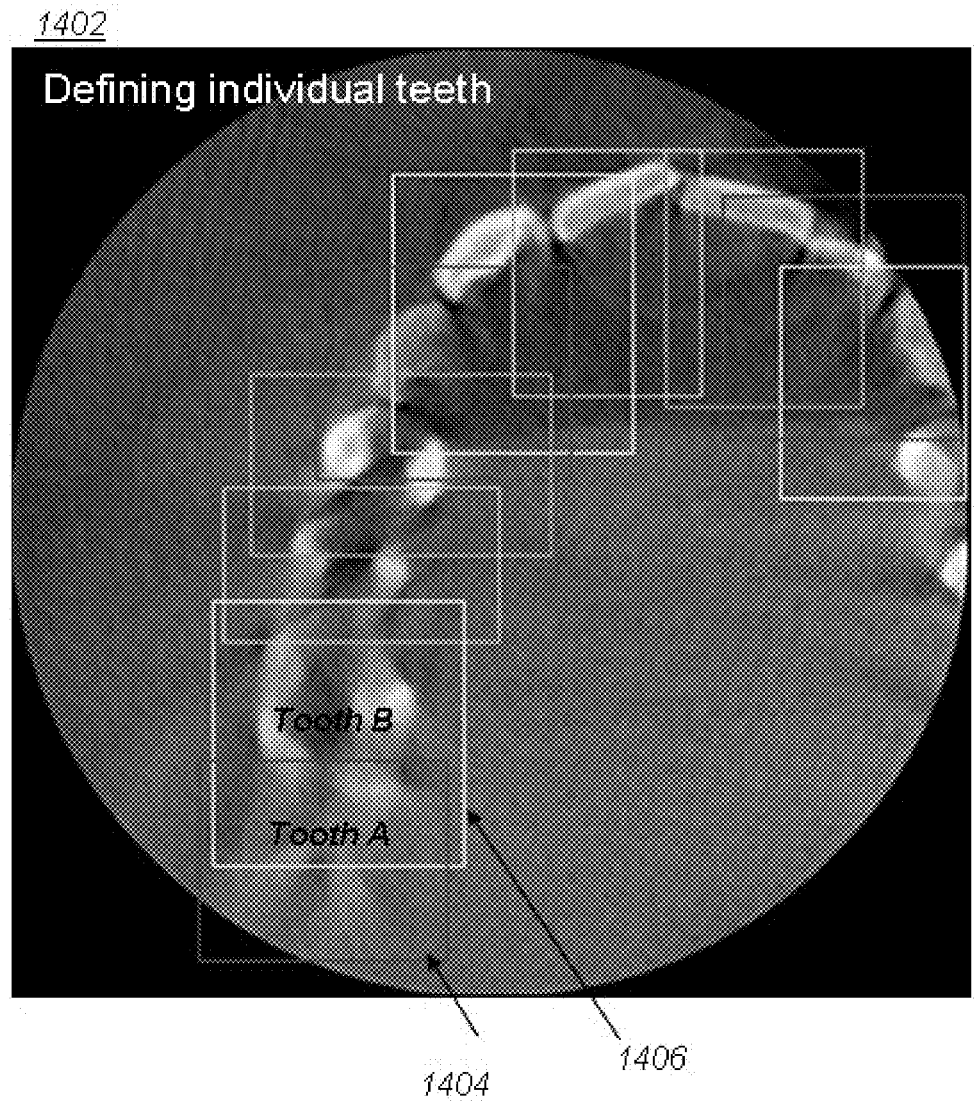
FIG. 14 shows the image of FIG. 11B with individual teeth defined and outlined.

For the example image shown in FIG. 13, the axial view of bounding cubes is shown in an image 1402 in FIG. 14. With reference to both FIGS. 13 and 14, a rectangle 1404 for Tooth A is determined by separation curves 1304 and 1306. A rectangle 1406 for Tooth B is determined by separation curves 1308 and 1310. Again, rectangle 1404 is an axial view of the bounding cube that provides a sub-volume for segmentation of Tooth A, the height of the bounding cube for Tooth A is the average teeth height estimated in step 1006 (FIG. 10). Similarly, rectangle 1406 is an axial view of the bounding cube that provides the sub-volume for segmentation of Tooth B, the height of the bounding cube for Tooth B is the average teeth height estimated in step 1006. In a tooth volume definition step 1012 in FIG. 10, these bounding cubes define individual teeth volumes, or sub volumes, to be used in subsequent segmentation processing.

Following the steps for defining a tooth volume (or sub volume) the segmentation process of a tooth object of interest is carried out in the FIG. 10 sequence in a seed generation step 1014 and a segmentation step 1016. For segmentation, a sub volume SV is presented to an image processing algorithm; this may be a bounding cube as previously described. The image processing algorithm in step 1014 then provides labeling hints, such as seeds, to a segmentation algorithm. The algorithms in step 1014 can be a combination of filtering, edge detection, pattern recognition, thresholding, morphological processing, classification, line detection, ellipse detection, image masking, or other steps for generating foreground and background seeds that provide initial definition of foreground (tooth) from background data. With this data provided as foreground and background seeds, for example, region growing logic can be applied to the overall image as an initial part of the segmentation process. Region growing using seed data as labeling hints is an image segmentation method that is well known to those skilled in the image segmentation arts.

Figure 15:
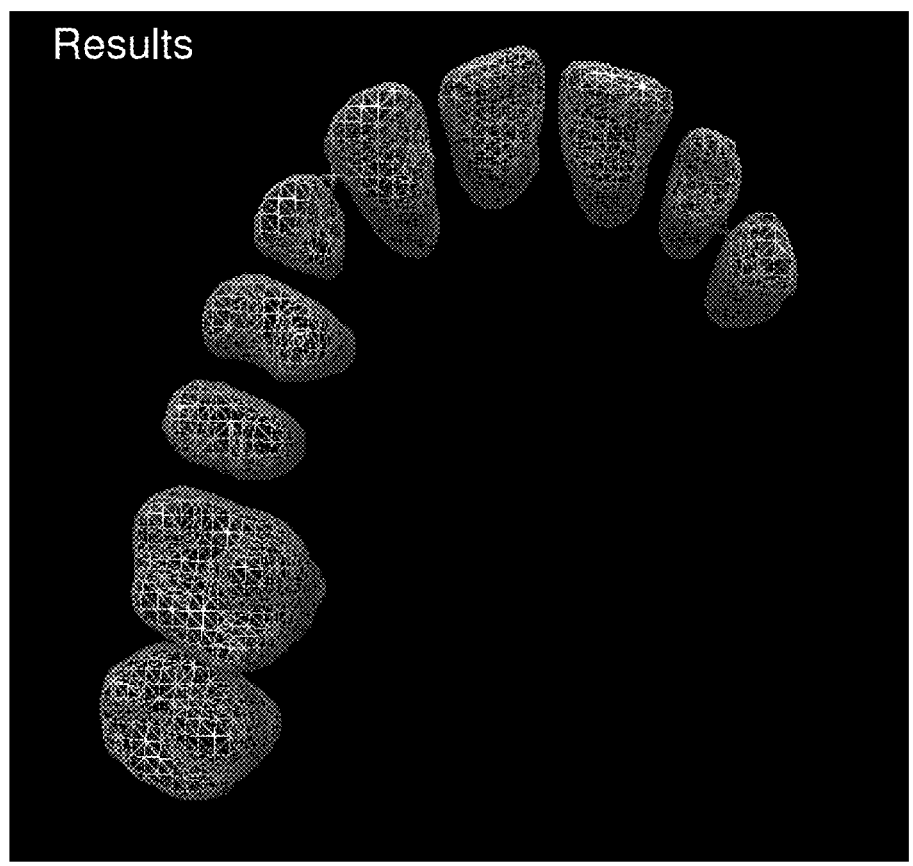
FIG. 15 shows segmented teeth using an embodiment of the present invention.

The exemplary labeling hints that are generated for seed generation step 1014 can contain location or position hints for objects of interest (tooth voxels in this context) instead of or in addition to image intensity hints for objects of interest. In addition, these hints can also include location hints for background content, or objects of noninterest, image intensity hints for objects of noninterest, and other related content. Segmentation methods for teeth and other structures using various types of labeling hints are well known to those skilled in the dental image analysis arts. A segmentation algorithm such as the method disclosed in commonly assigned US Patent Application Publication No. US2012/0313941 by Li et al, entitled "System and method for high speed digital volume processing", incorporated herein by reference in its entirety, can be used. Segmentation can be applied in step 1016 to segment one or more teeth, or parts of a tooth or teeth. FIG. 15 shows an exemplary tooth segmentation result of an embodiment of the present invention in an image 1502.

In general, the results of step 1016 are presented to the user in a graphical display, either two dimensionally or three dimensionally. These results may be presented as optional, for approval by the operator, for example. The user has an option to modify the results by adding or removing labeling hints (such as by editing parameters) and resubmitting the hints to step 1016 for another round of segmentation. Threshold values for pixel or voxel intensity, for example, can be edited for either foreground (tooth) or background content. This process can be repeated a plurality of times until the user is satisfied with the segmentation results.

Figure 16:
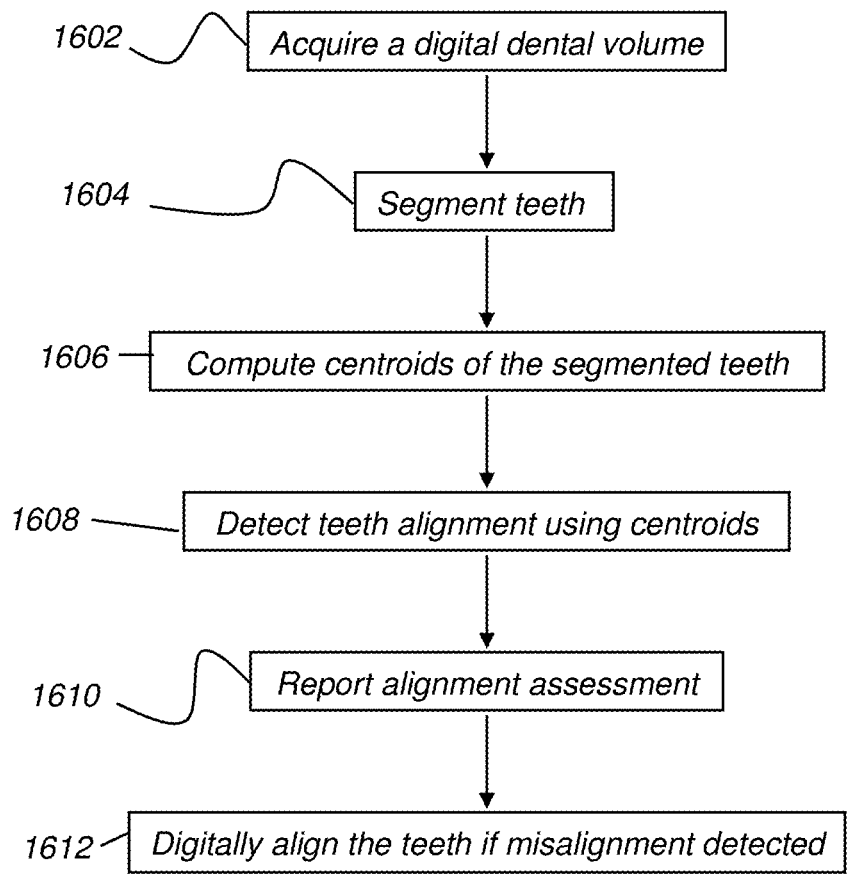
FIG. 16 is a logic flow diagram that shows a sequence of steps for reporting alignment assessment.

Now referring to FIG. 16 there is shown a flowchart that describes the steps of teeth alignment detection of the present invention. A digital dental volume such as a CBCT volume is acquired in a data acquisition step 1602. A teeth segmentation step 1604 performs tasks similar to previously described steps 1004 through 1016 of FIG. 10 to obtain a set of segmented teeth for either upper jaw or lower jaw as shown in FIG. 15.

Figure 17:
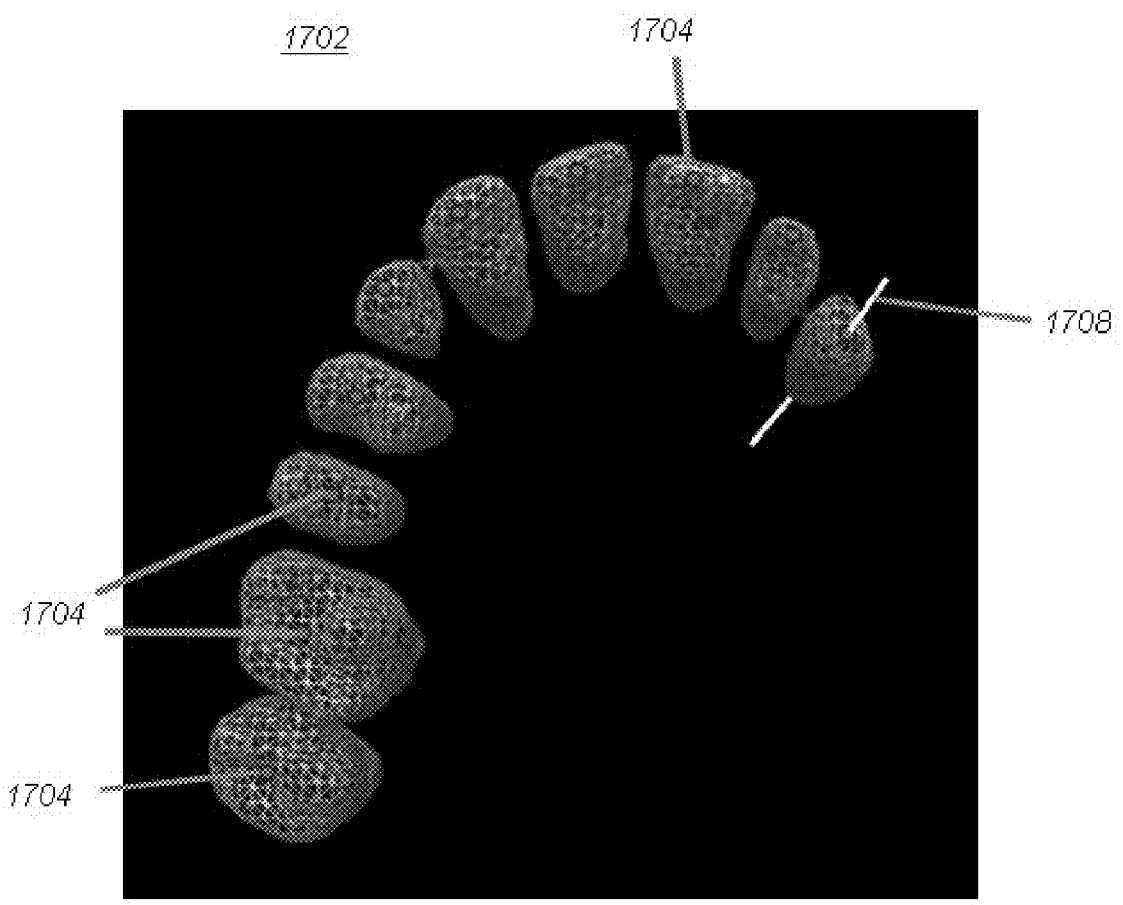
FIG. 17 shows the segmented teeth of FIG. 15 with centroids identified.

In a centroid computation step 1606, the positions of centroids of segmented teeth are computed. FIG. 17 shows an image 1702 with exemplary centroids 1704. Here, a centroid 1704 of a tooth is the intersection point of a tooth crown surface and a tooth principal axis 1708, as shown in FIG. 17. A principal axis is one of the eigenvectors computed using the 3D positions of all or part of the voxels of a tooth and the code values of all or part of the voxels of a tooth. Alternately, the centroid of a tooth can also be computed as the center of inertia, alternately termed the inertia center, of a segmented tooth, or the inertia center of the crown part of a tooth, that portion above the gum line. The inertia center computation takes into account differences in mass for tooth content as well as surface shape characteristics. A centroid of a tooth can alternately be computed as the spatial center or 3D geometric center of a segmented tooth, or as the geometric center or approximate geometric center of the crown portion of a tooth. Thus, it can be seen that there are a number of alternative ways to calculate the centroid for a segmented tooth. According to an embodiment of the present invention, the same centroid computation is used for each of the segmented teeth, whether the centroid is considered as the intersection of the tooth principal axis with the surface of the crown, the inertia center of the tooth or tooth crown portion, or the spatial or 3D geometric center of the tooth or tooth crown portion. That is, provided that the centroid for each tooth in a set of teeth is computed in the same way, the pattern of centroids for the set of teeth can be analyzed and used, as described subsequently. Methods for eigenvector, inertia center, and tooth centroid computation are well known to those skilled in the orthodontic measurement, cephalometric, and evaluation arts and are applied, for example, in using a number of methods used for orthodontics and cephalometric assessment.

Figure 18:
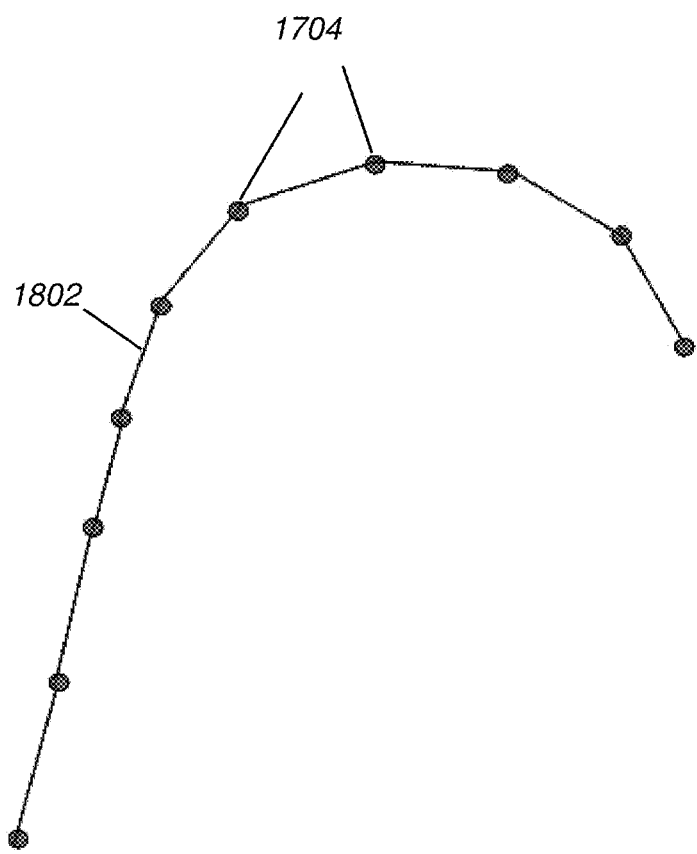
FIG. 18 shows an arrangement of tooth centroids that conforms to a convex hull.

The centroids computed in step 1606 are subject to alignment assessment in an alignment detection step 1608. In general, centroids of a set of teeth, either upper teeth or lower teeth, provide spatial reference points that define extreme points of a convex hull, as the term is understood to those skilled in the imaging analysis arts. Extreme points are points that lie along the boundary of the convex hull. In practice, the convex hull defines a smooth unbroken curve that changes direction predictably, and does not have sudden indented or out-dented portions. In a convex hull construction, a straight line connecting any two points within the convex hull also lies fully within the convex hull. FIG. 18 shows a convex hull 1802 defined by a number of centroids 1704. According to an embodiment of the present invention, if all of the centroids of the set of three or more teeth teeth (either upper or lower jaw) lie along a convex hull as shown in FIG. 18, then the set of teeth are considered to be aligned. Convex hull conformance is thus used to help identify tooth misalignment.

Figure 19:
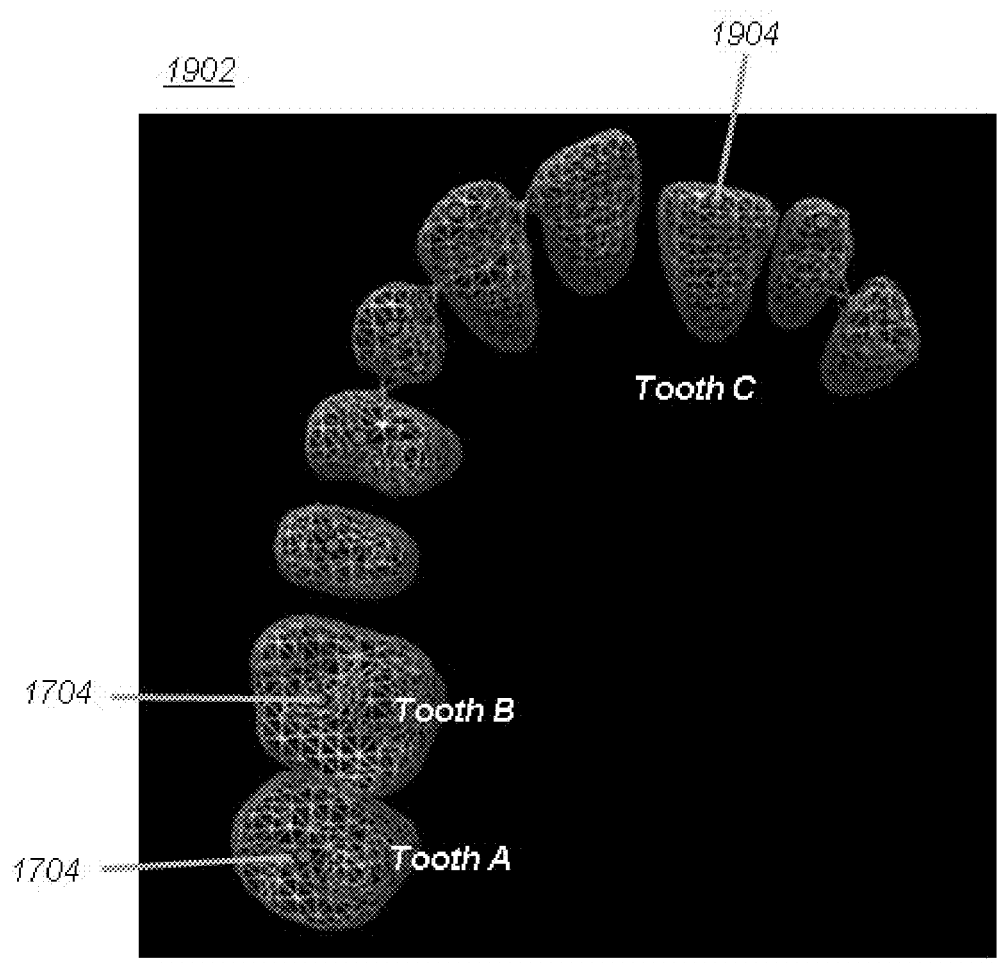
FIG. 19 shows segmented teeth with centroids identified.
Figure 20:
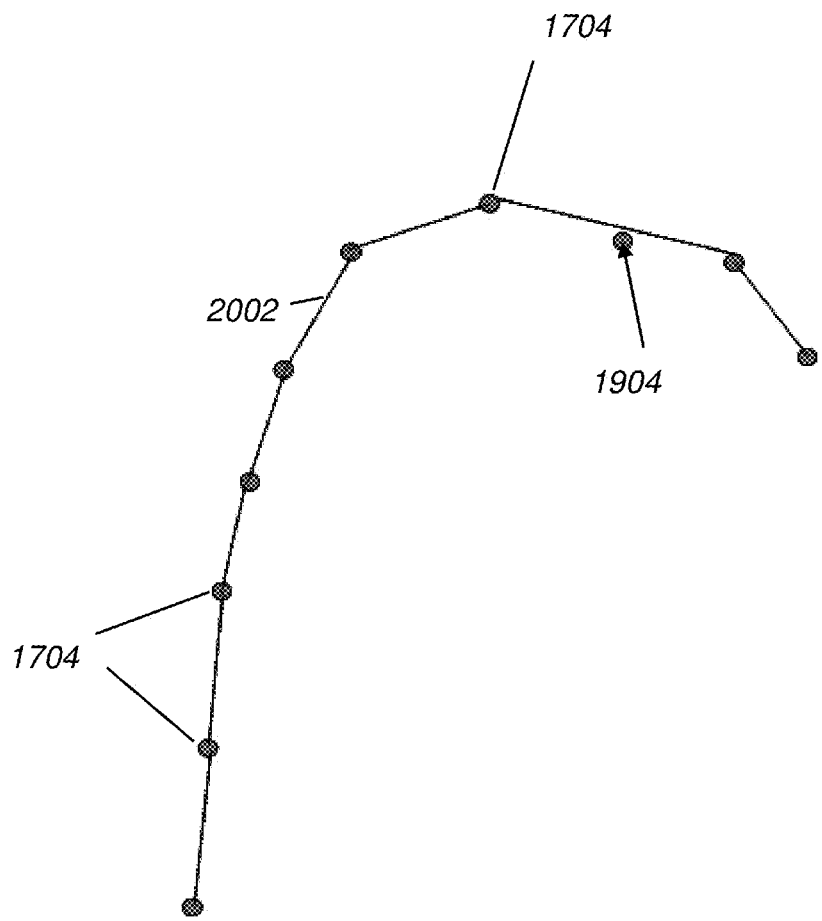
FIG. 20 shows an arrangement of tooth centroids that do not conform to a convex hull.

FIG. 19 shows an image 1902 with an exemplary misaligned set of teeth. FIG. 20 shows only the centroids 1704 and 1904 of these teeth. Tooth C, with its centroid 1904, is noticeably shifted from its original position, such as is shown in FIG. 17. Applying convex hull detection algorithm to this altered set of centroids reveals that centroid 1904 is no longer an extreme point of a convex hull 2002 as shown in FIG. 20.

According to an embodiment of the present invention, if one or more of the centroids are not extreme points of a convex hull, mis-alignment is detected for a particular set of teeth. In the workflow of FIG. 16, the assessment results are reported to the user in a reporting step 1610. This condition is reported by a display of teeth and centroids, for example, with the centroids that fail to meet the convex hull criterion highlighted on the display screen. The user can then digitally manipulate the one or more mis-aligned teeth through a graphical user interface (not shown) in order to shift the position of the misaligned tooth towards or away from alignment (step 1612). The computer algorithm then repeats step 1608 in real time and reports the results. For FIG. 19, for example, an operator interface instruction, entered using a mouse, a keyboard arrow key, or a touch screen, incrementally shifts the position of the misaligned tooth toward a more suitable, aligned position. Alternately, system software automatically shifts the position of a centroid that is indicative of misalignment, moving the centroid and its corresponding tooth on the display until an improved alignment is achieved.

Embodiments of the present invention provide methods for assisting the dental practitioner in assessing tooth misalignment using volume image data. By computing and using centroids of segmented teeth, these methods provide a straightforward way to present alignment information to the viewer.

According to an embodiment of the present invention, a computer program has stored instructions that process image data accessed from an electronic memory in accordance with the method described. As can be appreciated by those skilled in the image processing arts, a computer program of an embodiment of the present invention can be utilized by a suitable, general-purpose computer system, such as a personal computer or workstation. However, many other types of computer systems can be used to execute the computer program of the present invention, including networked processors. The computer program for performing the method of the present invention may be stored in a computer readable storage medium. This medium may comprise, for example; magnetic storage media such as a magnetic disk (such as a hard drive) or magnetic tape; optical storage media such as an optical disc, optical tape, or machine readable bar code; solid state electronic storage devices such as random access memory (RAM), or read only memory (ROM); or any other physical device or medium employed to store a computer program. The computer program for performing the method of the present invention may also be stored on computer readable storage medium that is connected to the image processor by way of the internet or other communication medium. Those skilled in the art will readily recognize that the equivalent of such a computer program product may also be constructed in hardware.

It will be understood that the computer program product of the present invention may make use of various image manipulation algorithms and processes that are well known. It will be further understood that the computer program product embodiment of the present invention may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present invention, are not specifically shown or described herein and may be selected from such algorithms, systems, hardware, components and elements known in the art.

The invention has been described in detail with particular reference to presently preferred embodiments, but it will be understood that variations and modifications can be effected that are within the scope of the invention. For example, geometric shapes entered by the operator may have a default shape, such as a rectangle of a predefined size. Operator instructions or overrides can be entered in any of a number of ways. Volume image data can be obtained from CBCT and visible light imaging. The presently disclosed embodiments are therefore considered in all respects to be illustrative and not restrictive. The scope of the invention is indicated by the appended claims, and all changes that come within the meaning and range of equivalents thereof are intended to be embraced therein.

The invention claimed is:

1. A method of automatic tooth segmentation, the method executed at least in part on a computer system and comprising:
   acquiring volume image data for either or both upper and lower jaw regions of a patient;
   identifying image content for a specified jaw from the acquired volume image data and, for the specified jaw:
   (a) estimating an average tooth height for teeth within the specified jaw;
   (b) finding a jaw arch region;
   (c) detecting one or more separation curves between teeth in the jaw arch region;
   (d) defining at least one individual tooth sub volume according to the estimated average tooth height and the detected separation curves; and
   (e) segmenting at least one tooth from within the defined sub-volume; and
   displaying, storing, or transmitting the volume image data for the at least one segmented tooth.

2. The method of claim 1 wherein segmenting the at least one tooth comprises generating foreground and background seeds for the at least one tooth.

3. The method of claim 1 further comprising defining and displaying a centroid position for the at least one segmented tooth.

4. The method of claim 3 further comprising defining and displaying two or more additional centroid positions for segmented teeth in the specified jaw and highlighting one or more displayed centroid positions that are indicative of tooth misalignment.

5. The method of claim 3 wherein defining and displaying two or more additional centroid positions comprises identifying an inertia center of at least a portion of the segmented tooth.

6. The method of claim 3 wherein defining and displaying two or more additional centroid positions comprises identifying a geometric center of at least a portion of the segmented tooth.

7. The method of claim 4 further comprising identifying tooth misalignment according to a convex hull conformance of the displayed centroid positions.

8. The method of claim 1 wherein acquiring volume image data comprises acquiring cone beam computed tomography image data.

9. The method of claim 1 wherein finding the jaw arch region comprises using adaptive thresholding.

* * * * *